United States Patent
Tamaki et al.

(10) Patent No.: US 7,198,600 B2
(45) Date of Patent: Apr. 3, 2007

(54) BODY TEMPERATURE MANAGING METHOD AND DEVICE, STORAGE MEDIUM, BODY TEMPERATURE MANAGING SYSTEM, AND PROGRAM

(75) Inventors: Yuko Tamaki, Tokyo (JP); Masae Oba, Kanagawa (JP); Junko Kawanishi, Kanagawa (JP); Kanako Hashimoto, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 615 days.

(21) Appl. No.: 09/867,614

(22) Filed: May 31, 2001

(65) Prior Publication Data

US 2002/0016553 A1 Feb. 7, 2002

(30) Foreign Application Priority Data

| Jun. 13, 2000 | (JP) | 2000-176734 |
| Jun. 13, 2000 | (JP) | 2000-176735 |
| Jun. 13, 2000 | (JP) | 2000-176983 |
| Jun. 13, 2000 | (JP) | 2000-176984 |

(51) Int. Cl.
*A61B 5/00* (2006.01)

(52) U.S. Cl. ............ 600/300; 600/301; 600/549; 128/903; 128/905; 128/920; 705/1; 705/3; 705/4

(58) Field of Classification Search ........ 600/300–301, 600/549; 128/903–905, 920; 705/2–4; 340/573.1; 379/106.1–106.2
See application file for complete search history.

(56) References Cited

U.S. PATENT DOCUMENTS

| 5,673,692 A | * | 10/1997 | Schulze et al. ............. 600/300 |
| 6,302,844 B1 | * | 10/2001 | Walker et al. .............. 600/300 |
| 6,443,890 B1 | * | 9/2002 | Schulze et al. ............. 600/300 |
| 6,478,736 B1 | * | 11/2002 | Mault ......................... 600/300 |
| 2002/0077953 A1 | * | 6/2002 | Dutta .......................... 705/37 |

FOREIGN PATENT DOCUMENTS

| JP | 03-218727 | 9/1991 |
| JP | 04-071531 | 3/1992 |
| JP | 04-096731 | 3/1992 |
| JP | 05-056936 | 3/1993 |
| JP | 05-228131 | 9/1993 |
| JP | 5-296851 | 11/1993 |
| JP | 9-122132 | 5/1997 |
| JP | 09-153096 | 6/1997 |
| JP | 10-033486 | 2/1998 |
| JP | 10-085223 | 4/1998 |
| JP | 10-143573 | 5/1998 |
| JP | 11-84036 | 3/1999 |
| JP | 11-316161 | 11/1999 |
| JP | 2000-008444 | 1/2000 |
| JP | 2000-031956 | 1/2000 |
| JP | 2000-093396 | 4/2000 |
| JP | 2000-175872 | 6/2000 |
| WO | 99/56629 | 11/1999 |

* cited by examiner

*Primary Examiner*—Max F. Hindenburg
*Assistant Examiner*—Michael C Astorino
(74) *Attorney, Agent, or Firm*—Fitzpatrick, Cella, Harper & Scinto

(57) ABSTRACT

Data measured by a thermometer is temporarily stored in a connection terminal, then transmitted to a server from the connection terminal via a network, and stored. The server makes analyses based on the stored temperature data, and transmits the analysis results. Thus, a body temperature managing and analyzing method, providing information unobtainable with a thermometer alone, can be provided by managing and analyzing body temperature over a network.

32 Claims, 28 Drawing Sheets

FIG. 6
MEMBERSHIP APPLICATION DEVICE DESCRIPTION 1
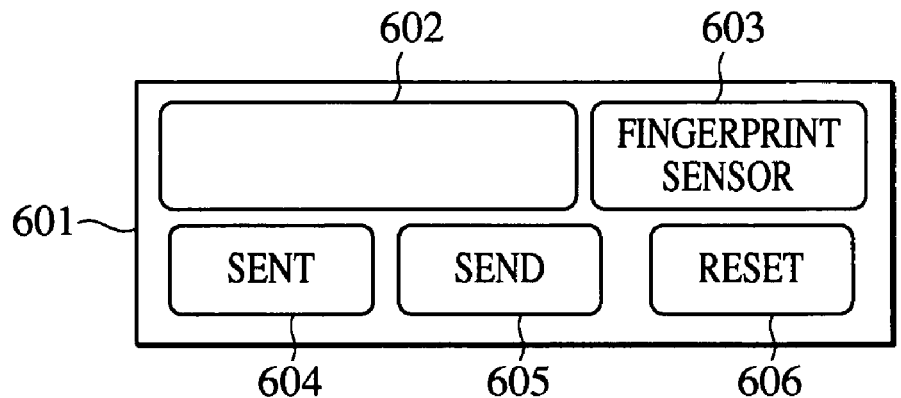
MEMBERSHIP APPLICATION DEVICE DESCRIPTION 2
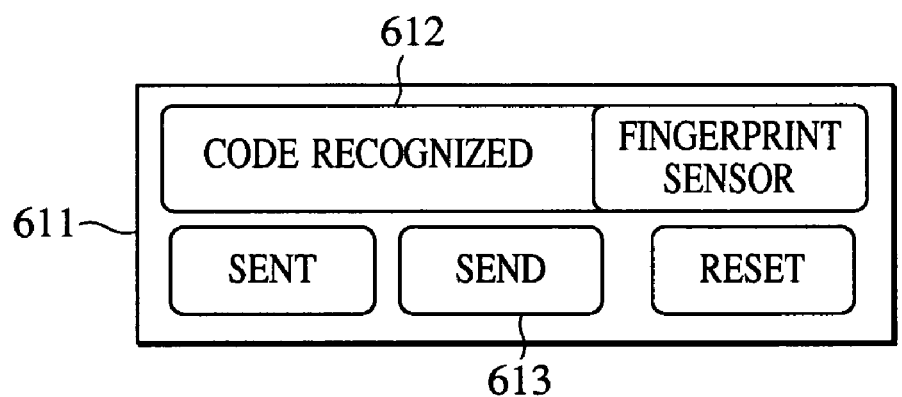
MEMBERSHIP APPLICATION DEVICE DESCRIPTION 3
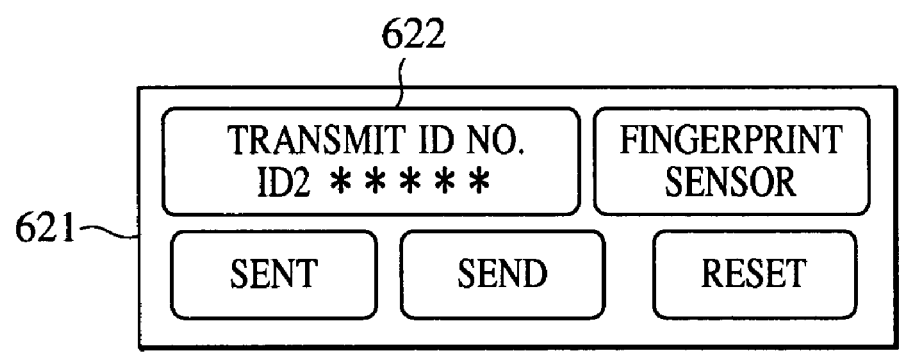

FIG. 19

DOCTOR ADVICE DATA

* IN ORDER TO RECEIVE ACCURATE DOCTOR ADVICE, YOU NEED TO DISCLOSE YOUR BASAL BODY TEMPERATURE DATA TO THE DOCTOR.

DO YOU WANT TO DISCLOSE ?

[YES] [NO] — 1901

* IN ORDER TO DISCLOSE YOUR BASAL BODY TEMPERATURE DATA, YOU NEED TO SEND YOUR DECIPHERING KEY.

DO YOU WANT TO SEND ?

[YES] [NO] — 1902

* INPUT YOUR DECIPHERING KEY.

[          ]   [OK]
               [Cancel] — 1903

OK TO TRANSMIT DECIPHERING KEY ?

[YES] [NO] — 1904

HOSPITAL LIST  FIG. 23

*WHICH STATE DO YOU WANT TO VIEW LIST OF HOSPITALS FOR ?

[ ] STATE

2301

*CLICK ON A DISTRICT

[CITY A] [TOWN D] ...............
[CITY B] [TOWN E] ...............
[CITY C] [TOWN F] ...............

2302 e.g.

CLICK ON A HOSPITAL THAT YOU WANT TO VIEW

[HOSPITAL A]
[CLINIC B]
[HOSPITAL C]
[ · ]
[ · ]
[ · ]
[ · ]

2303 e.g.

CLICK ON THE RESERVATION BUTTON IF YOU WANT TO MAKE A RESERVATION

· HOSPITAL A
   LOCATION
   HOURS
   ETC.
   ·
   ·
   ·

[RESERVATION]

2304

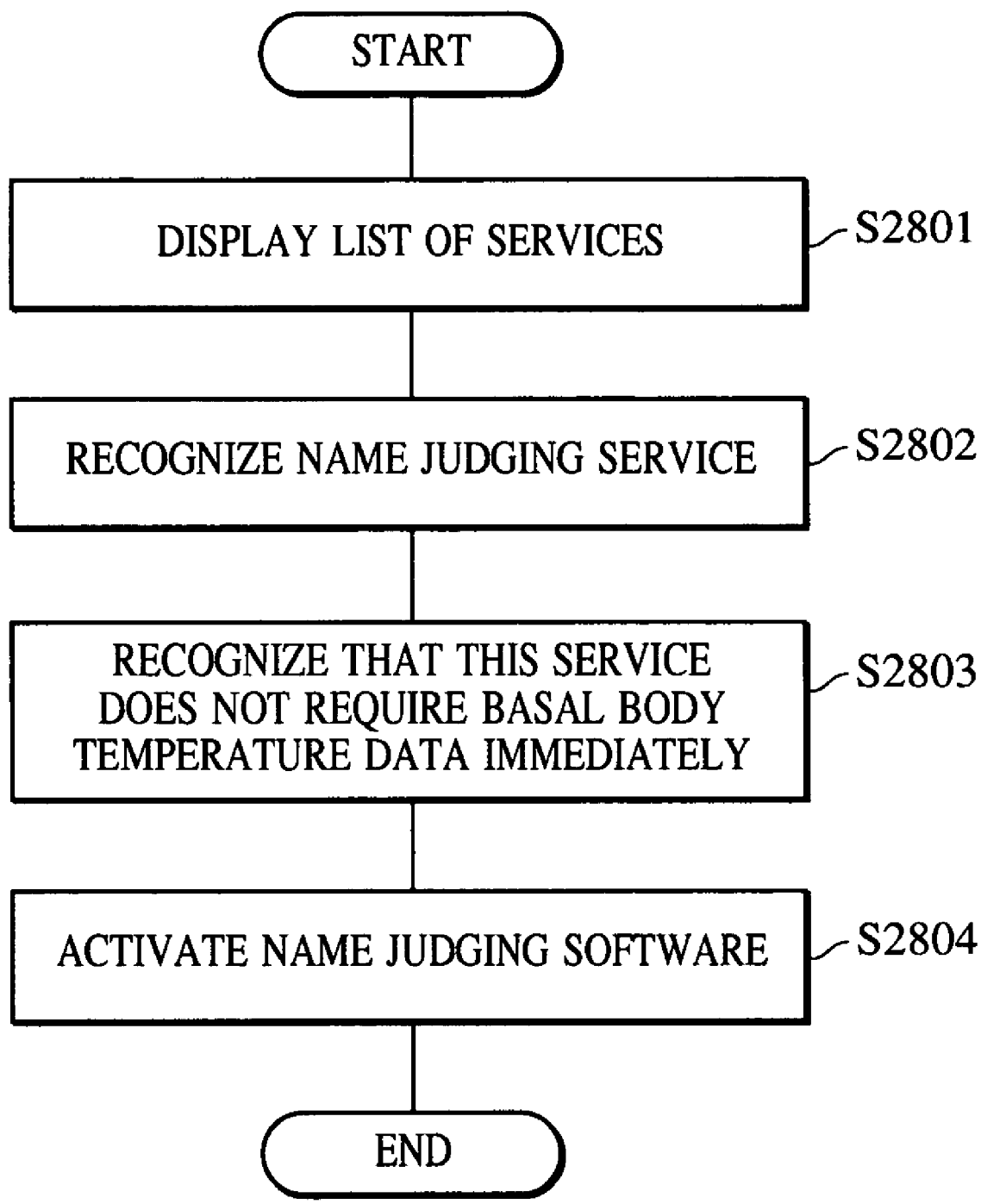

BODY TEMPERATURE MANAGING METHOD AND DEVICE, STORAGE MEDIUM, BODY TEMPERATURE MANAGING SYSTEM, AND PROGRAM

BACKGROUND OF THE INVENTION

1. Field of the Invention

The present invention relates to a method and a device for managing body temperature, a storage medium thereof, a system for managing body temperature, and a program thereof.

2. Description of the Related Art

Conventionally, in the event of a subject using a so-called gynecological thermometer to measure basal body temperature, wherein the subject simply measures the basal body temperature by placing the thermometer under the underarm or in the mouth in a resting state, the subject must fill out a graph following taking the basal body temperature, and items such as ovulation, infertile period, fertile period, menstruation, etc., are predicted based on complicated calculations which necessitate information known to the subject. There have also been methods for predicting or graph displaying of ovulation, infertile period, fertile period, menstruation, etc., in Japanese Patent Laid-Open No. 11-316161 (gynecological thermometer), Japanese Patent Laid-Open No. 11-84036 (wristwatch for notifying ovulation), Japanese Patent Laid-Open No. 5-296851 (body temperature managing system), Japanese Patent Laid-Open No. 9-122132 and the like, wherein body temperature measured in one way or another is sent to a terminal having storing means or control means, where judgment is made by the control means without necessitating judgement by the user.

However, advances in science have made it clear that information obtained by taking such basal body temperature can be used for not only the conventionally analyzed items, but also for items such as anovulation, periods wherein dieting is effective, body conditions such as skin conditions, and so forth, and accordingly, the knowledge of the subject and control means within a terminal of the subject may very well be insufficient for making judgment regarding such items. Moreover, such issues should preferably be judged by analysis made on the newest information.

Another problem has been that, even in the event that the subject does take basal body temperature, the subject often does not have the time to actually go to the hospital each time there is some change in the information obtained thereby, and further, even in the event that the subject might have the time, the subject has to go to a gynecologist to have the diagnosis made, which is in itself a factor why many individuals tend to postpone analysis.

Also, while managing individual information on the Internet is advantageous from the perspective of obtaining information, concerns over private information leaking out are always-present. Basal body temperature is information which requires particular protection, and leakage of the data on a network is a matter of concern.

SUMMARY OF THE INVENTION

Accordingly, it is an object of the present invention to solve the above problems, and provide management and analysis over a network to obtaining information difficult to obtain by basal body temperature alone.

Another object of the present invention is to provide judgment and medical analysis based on the newest analysis of the data of the subject, and to provide various services relating to basal body temperature data, by managing and analyzing the basal body temperature using a network.

Another object of the present invention is to provide a system wherein individuals can receive diagnosis based on measured basal body temperature without actually having to visit the hospital, under thorough management information to prevent leakage of the body temperature data of the subject in all steps, thereby completely protecting private data from external leakage.

To this end, according to a first embodiment of the present invention, a body temperature managing method comprises a body temperature data obtaining step for obtaining body temperature data, a body temperature data storing step for storing the body temperature data obtained in the obtaining step, a body temperature data analyzing step for analyzing the body temperature data based on the body temperature data stored in the storing step, and an analyzed data transmitting step for transmitting data that has been analyzed in said analyzing step.

Further objects, features and advantages of the present invention will become apparent from the following description of the preferred embodiments with reference to the attached drawings, in which like reference numerals designate the same or equivalent parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 6 is a diagram illustrating the display for application for membership;

FIG. 19 is a display screen for the doctor advice service;

FIG. 23 is a diagram illustrating a hospital list;

FIG. 28 is a diagram illustrating the flow of a name judging service.

DESCRIPTION OF THE PREFERRED EMBODIMENTS

The preferred embodiments of the present invention will now be described in detail with reference to the attached drawings.

Figure 1:
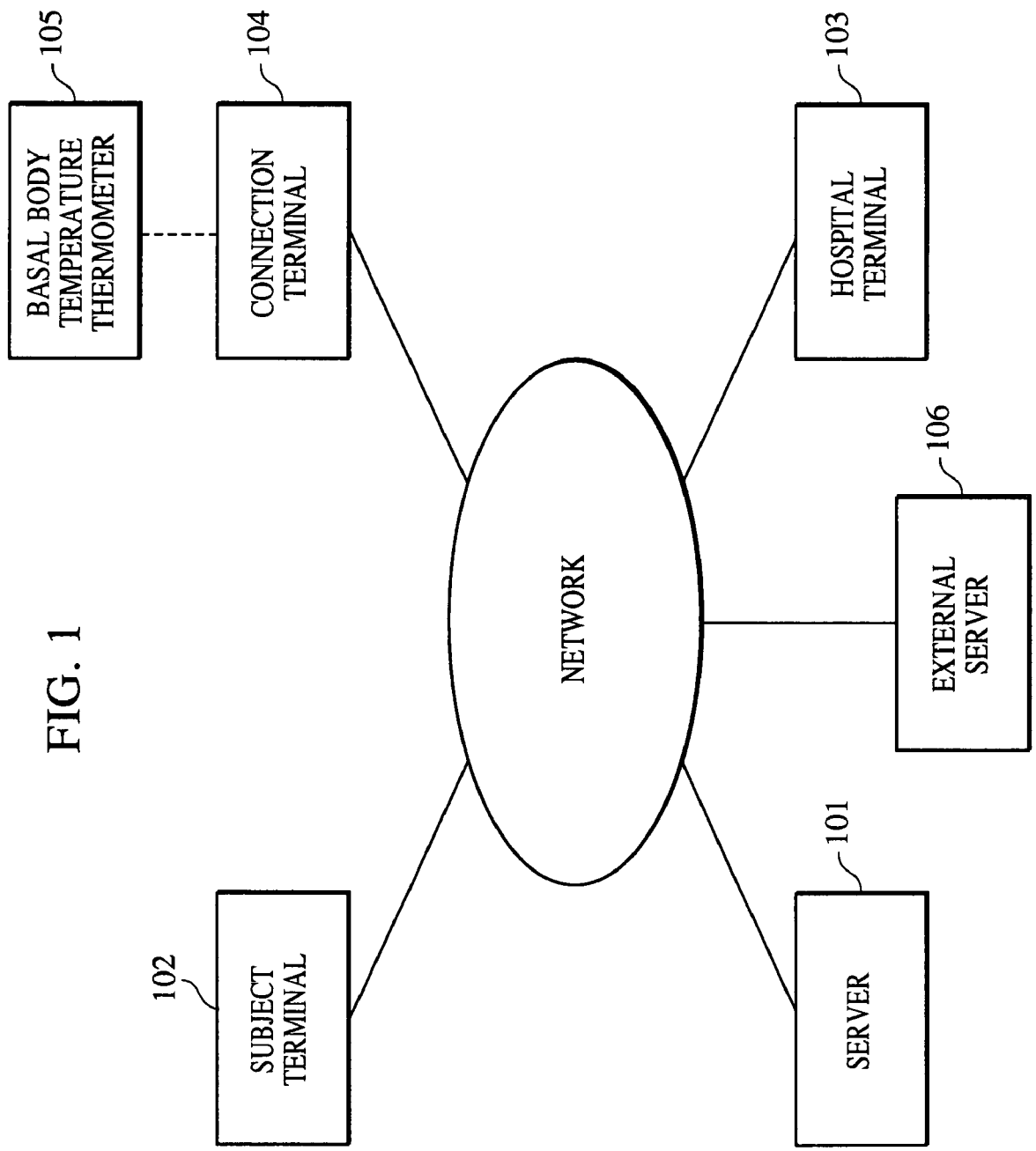
FIG. 1 is a diagram of the system configuration of an embodiment of the present invention.

FIG. 1 is a diagram illustrating a system configuration according to an embodiment of the present invention. Reference numeral 101 denotes a server computer (hereafter referred to simply as "server"), and 102 denotes a subject terminal. The subject terminal is a terminal necessary for the subject to receive the later-described various services, such as a personal computer, cellular phone, portable terminal, and so forth. Reference numeral 103 denotes a hospital terminal, 104 denotes a connection terminal for receiving basal body temperature data and transmitting this to a server, 105 denotes a basal body temperature thermometer, and 106 denotes an outside server which provides various services, such as a server of a service-providing corporation. The outside server is connected to the terminals via networks such as the Internet, and the connection terminal 104 and the basal body temperature thermometer perform wireless communication.

Figure 2:
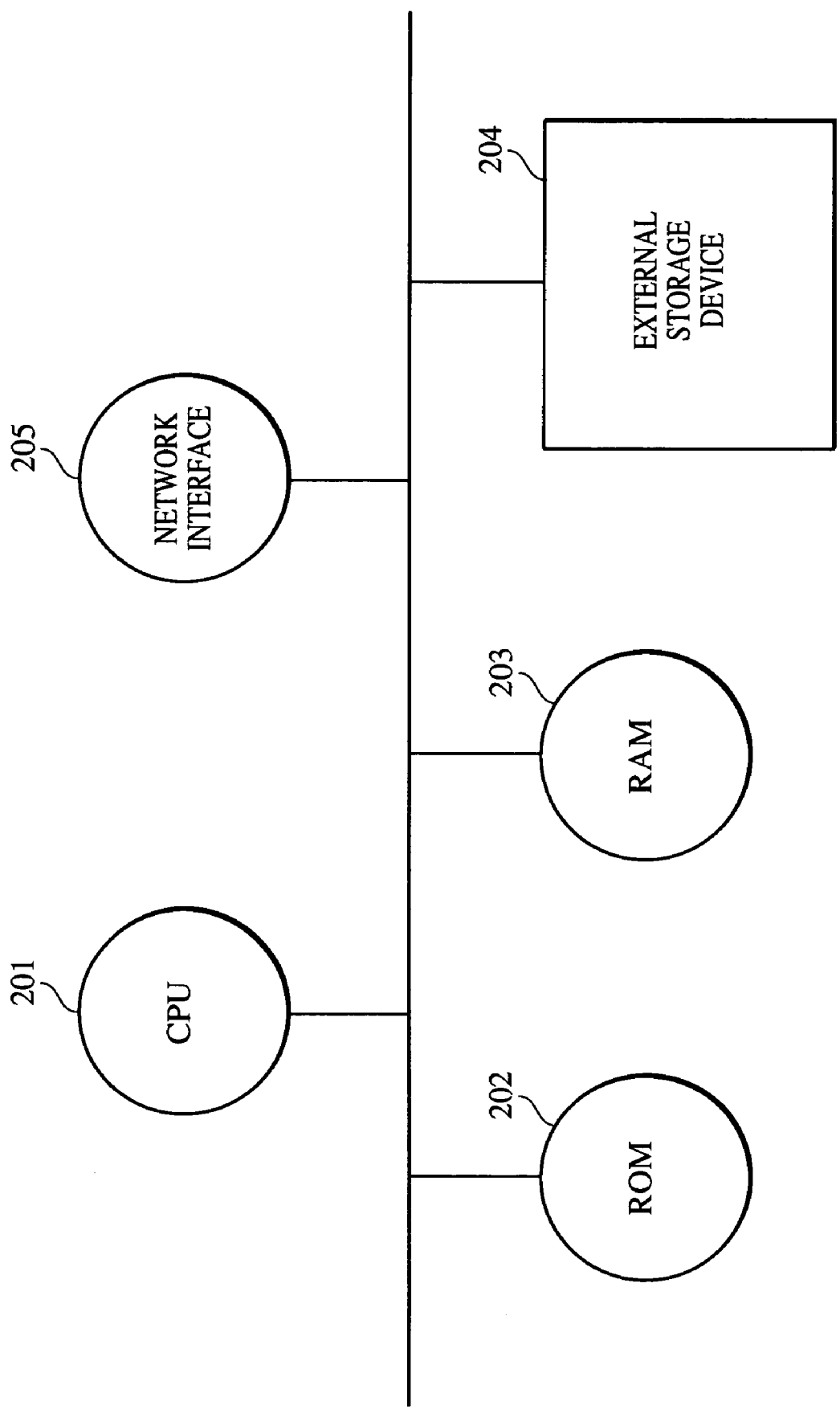
FIG. 2 is a block diagram illustrating the system configuration of a server.

FIG. 2 is a diagram illustrating the device configuration of the server 101 according to an embodiment of the present invention. The server 101 is made up of a CPU 201 which reads out a program and executes actual processing, ROM 202 which stores beforehand control means for the CPU 201, RAM 203 which the CPU 201 uses for executing the processing, an external storage device 204 which is a recording medium for supplying program code, a communication interface 205 used at the time of making connection to a network, and so forth.

Figure 3:
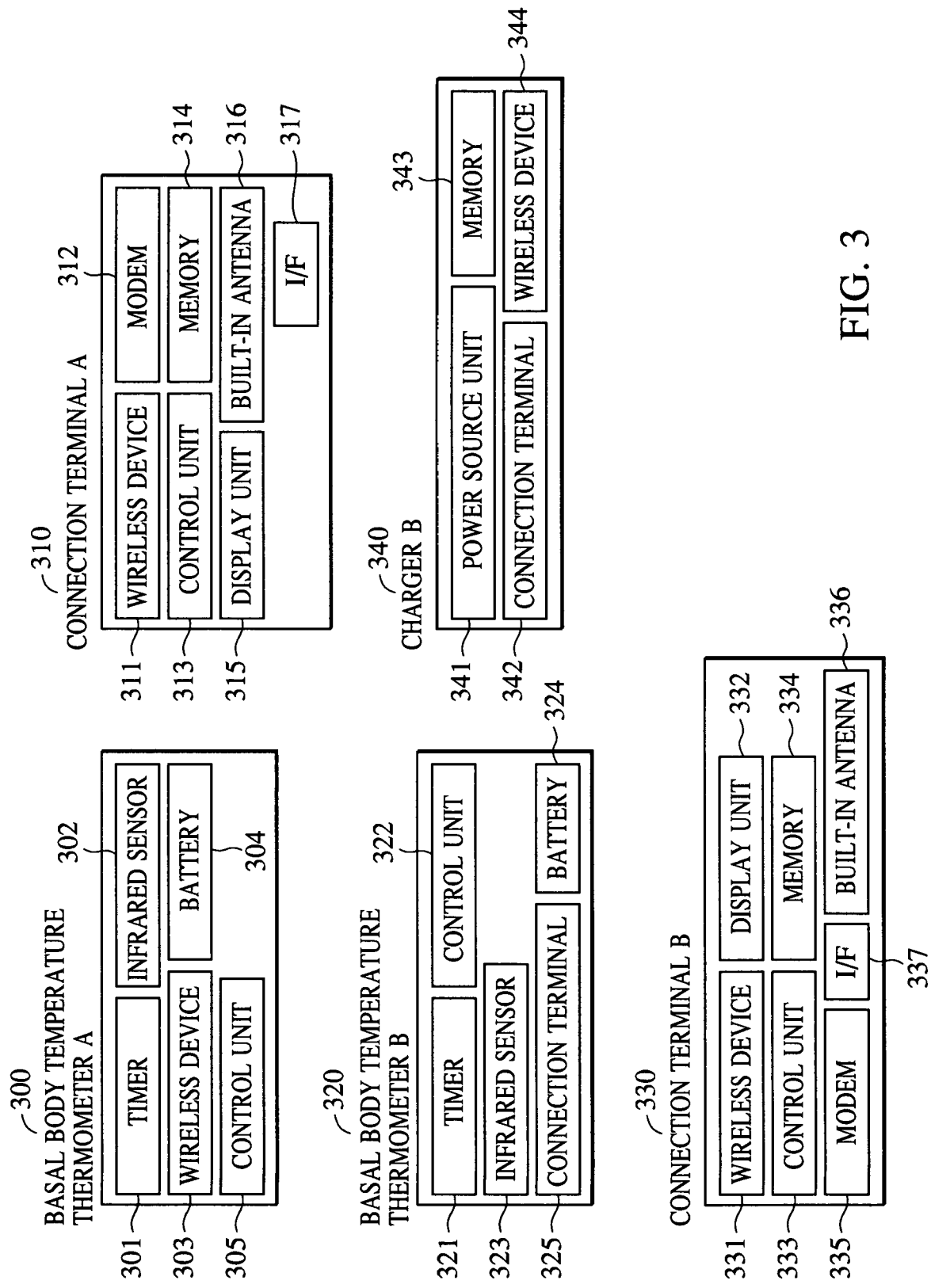
FIG. 3 is a block diagram illustrating the configuration of a basal body temperature thermometer and a connection terminal according to an embodiment of the present invention.

FIG. 3 is a block diagram illustrating the configuration of the basal body temperature thermometer and the connection terminal according to an embodiment of the present invention. With the basal body temperature thermometer and the connection terminal according to the embodiment of the present invention, the basal body temperature is measured while the subject is sleeping, in order to obtain a measurement more accurate than that of conventional basal body temperature measurements. Also, this lightens the load of taking measurements on the subject, which have been considered to be quite troublesome, and further the measured basal body temperature data can be enciphered to receive services from the server such as accumulation and analysis, via a telephone line. General specifications which are characteristic of the basal body temperature thermometer and the connection terminal according to the embodiment of the present invention will now be described with reference to FIG. 3.

Reference numeral 300 denotes a basal body temperature thermometer A which is an embodiment of the present invention. The basal body temperature thermometer A can be worn directly in the ear of the subject, and can be arranged to automatically measure the basal body temperature of the subject while sleeping. Reference numeral 301 denotes a timer, 302 denotes an infrared sensor, 303 denotes a wireless device, 304 denotes a battery, and 305 denotes a control unit. The timer 301 has clocking functions, and transmits the timing for measuring the basal body temperature to the control unit 305. The control unit 305 instructs the infrared sensor 302 to measure the basal body temperature, receives the measured basal body temperature from the infrared sensor 302, and transmits the measured basal body temperature to a connection terminal A 310 via the wireless device 303. Each of the processes are executed by receiving supply of electric power from the battery 304. The battery is preferably charged by electricity generated by light from fluorescent lamps or the like, as with conventional thermometers.

Reference numeral 310 denotes a connection terminal A which is an embodiment of the present invention. Reference numeral 311 denotes a wireless device, 312 denotes a modem, 313 denotes a control unit, 314 denotes memory, 315 denotes a display unit, 316 denotes a built-in antenna, and 317 denotes an interface. The control unit 313 obtains the basal body temperature received by the built-in antenna 316 via the wireless device, and instructs the basal body temperature to be stored in the memory 314. The memory 314 is capable of accumulating several days worth of measured data until a reset button is pressed, and the data can be transmitted as a batch to the server at a later time, thereby saving on the telephone bill for connecting to and accessing the server. The contents displayed on the display unit 315 will be described later. The interface 317 is an interface unit for connecting to a network, and data can be transmitted to the server from wire telephones, cellular phones, and so forth, via this interface 317.

Also, as a separate form of the basal body temperature thermometer according to the embodiment of the present invention, the basal body temperature thermometer may be a rechargeable type instead of having a wireless device in the portion mounted in the ear, taking into consideration the fact that the device is worn in the ear and that wireless devices may affect the human body. In this arrangement, reference numeral 340 denotes a charging mount which has a wireless device 344. Upon rising, the subject places the basal body temperature thermometer B on the charging mount B, and the wireless device 344 in the charging mount B transmits the basal body temperature data to the connection terminal B 330. Details of the basal body temperature thermometer B 320 and the connection terminal B 330 will be omitted here, since the details have already been described in the description of the basal body temperature thermometer A 300 and the connection terminal A 310. Note, however, that the basal body temperature thermometer B has a connection terminal 325 instead of the wireless device 303.

Also, using Bluetooth wireless technology for the wireless devices of the basal body temperature thermometer A 300 and the connection terminal A 310, and the basal body temperature thermometer B 320 and the connection terminal B 330, enables exchange of data to be performed only at close proximity and with secrecy, so leakage of data can be prevented. Also, using a connection terminal having such wireless devices allows remote control between various home appliances having the same wireless devices, and is not limited to basal body temperature.

Though the present embodiment is described as an arrangement wherein the basal body temperature thermometer is worn in the ear, arrangements may be used wherein the measurement is taken at the underarm or mouth as with conventional methods, and the means for transmitting the data may be via wire instead of wireless.

Also, the connection terminals A and B may be arranged so as to manage multiple basal body temperature thermometers with a single connection terminal, thereby allowing the connection terminal to be shared among sisters or family members, for example.

The following embodiment will be described with reference to an embodiment using a basal body temperature thermometer A 300 and a connection terminal A 310.

Figure 5:
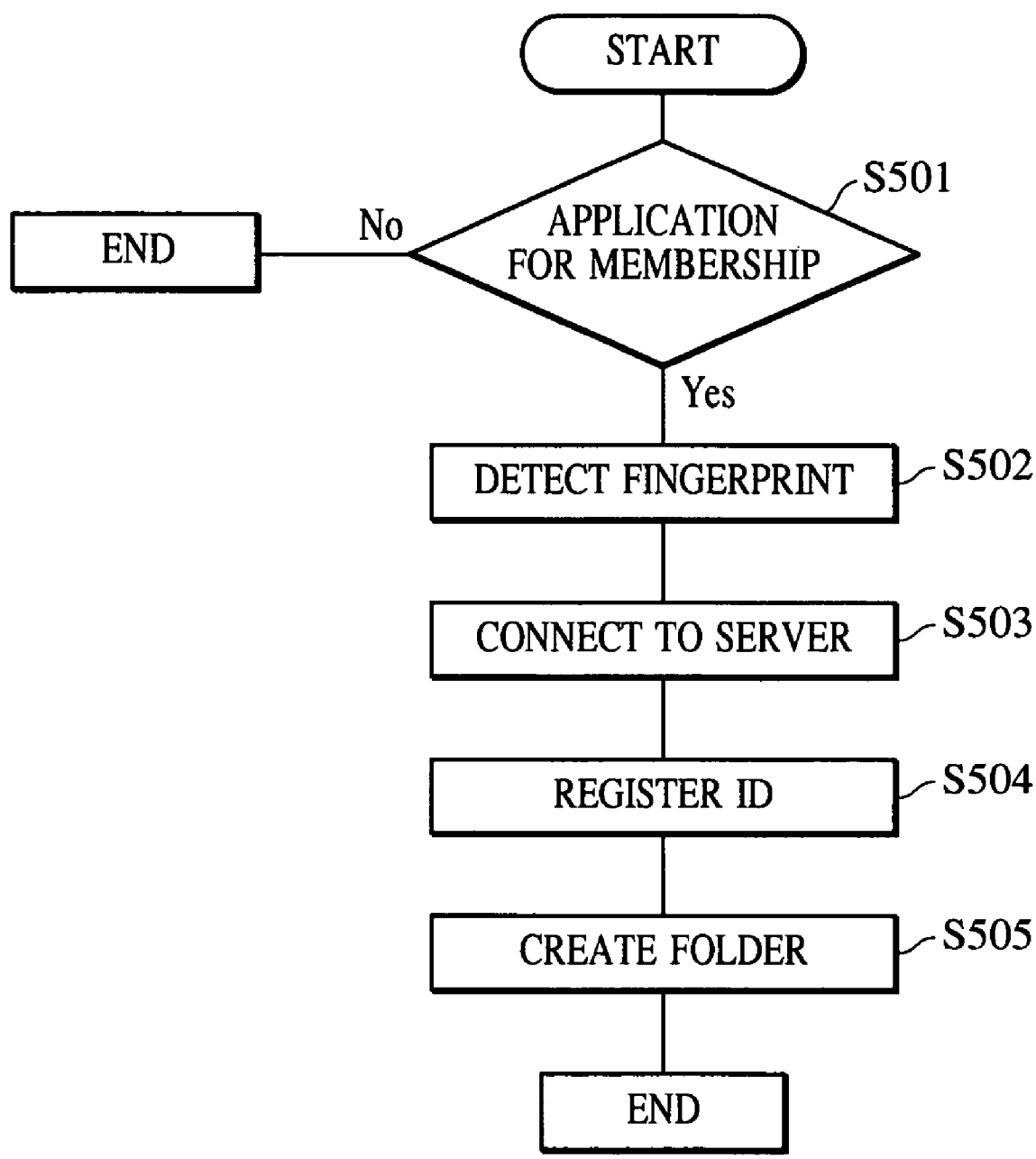
FIG. 5 is a diagram illustrating the flow for gaining membership using a fingerprint sensor.

The following is a description of the procedures for gaining membership with the basal body temperature thermometer A300 using a fingerprint sensor, and transmission of basal body temperature to the server, with reference to FIGS. 5 and 6. With the present embodiment, the subject performs fingerprint recognition at the time of registering the subject, since basal body temperature, which is data that requires protection, is going to be handled. Further, due to concerns of basal body temperature data leaking out on the network, the basal body temperature data is managed using digitized data read from the fingerprint sensor as identification of the subject. Subsequent services with this system are received using the enciphered digitized data read from the fingerprint sensor as the decoding key, so user registration and verification can be easily performed with simple operations. Further, registering an ID number provided to the connection terminal beforehand protects private information from external leakage. Also, though the present basal body temperature does serve as a basal body temperature thermometer whereby much information can be obtained using the server to manage basal body temperature, the thermometer can be used in the same manner as a conventional thermometer. In this case, the basal body temperature thermometer can be used as is without registration of the subject. Also, verification can be made by a conventional arrangement wherein a password or the like is used, rather than fingerprint identification.

FIG. 5 is a diagram illustrating the procedures for gaining membership using a fingerprint sensor, and FIG. 6 is a diagram illustrating the display screen of a touch panel for the procedures of gaining membership. The display screens denoted by reference numerals 601, 611, and 621 are screens displayed on the display units 315 and 332 of the connection terminals A and B. Reference numerals 602, 612, and 622 denote display portions for providing guidance of the procedures, 603 denotes a fingerprint sensor, 604 denotes a display unit for displaying that sending has been completed, 605 denotes a send button, and 606 denotes a reset button.

The procedures for applying for membership will be described following the flowchart shown in FIG. 5. In step S501, the subject first selects whether or not to receive services. Subjects who choose not to receive services can use the thermometer as a conventional basal body temperature thermometer, without applying for membership.

In the event that the subject selects application for membership in step S502, and places her finger on the fingerprint sensor 603 of the connection terminal A 300 for performing subject registration, the fingerprint is detected. Once the fingerprint is detected, the fingerprint read by the fingerprint sensor 603 is digitized at the control unit 313, and stored in the memory 314. The digitized data is then enciphered, thereby serving as a deciphering key necessary for receiving the later-described various services with the present system. Once the digitized data is stored in the memory 314, a message 612 notifying that subject recognition by the fingerprint sensor 603 has been completed is displayed on the display unit 315, and at the same time the send button and reset button are lit.

In step S503, pressing the send button 605 activates the interface 317, and the connection terminal A is connected to the server 101. Pressing the reset button 606 instead deletes the recognized data.

In step S504, once connection to the server 101 is established, the blinking of the reset button 606 stops, the send button 613 begins to blink, and the enciphered digitized data is transmitted. Following the transmission, the server 101 makes a reply in the form of a digitized data registration completion notification. When the completion notification is returned, a message (622 in FIG. 6) is displayed on the display unit 601, prompting the subject to send the ID No., provided beforehand to the connection terminal, to the server 101. Pressing the send button 605 again transmits the ID No., which is recognized at the server 101.

In step S505, once the ID is recognized at the server, the server creates a folder for the subject. After completions of the procedures, the sent button 604 is lit, and pressing the reset button 606 ends preparation for receiving services.

Figure 7:
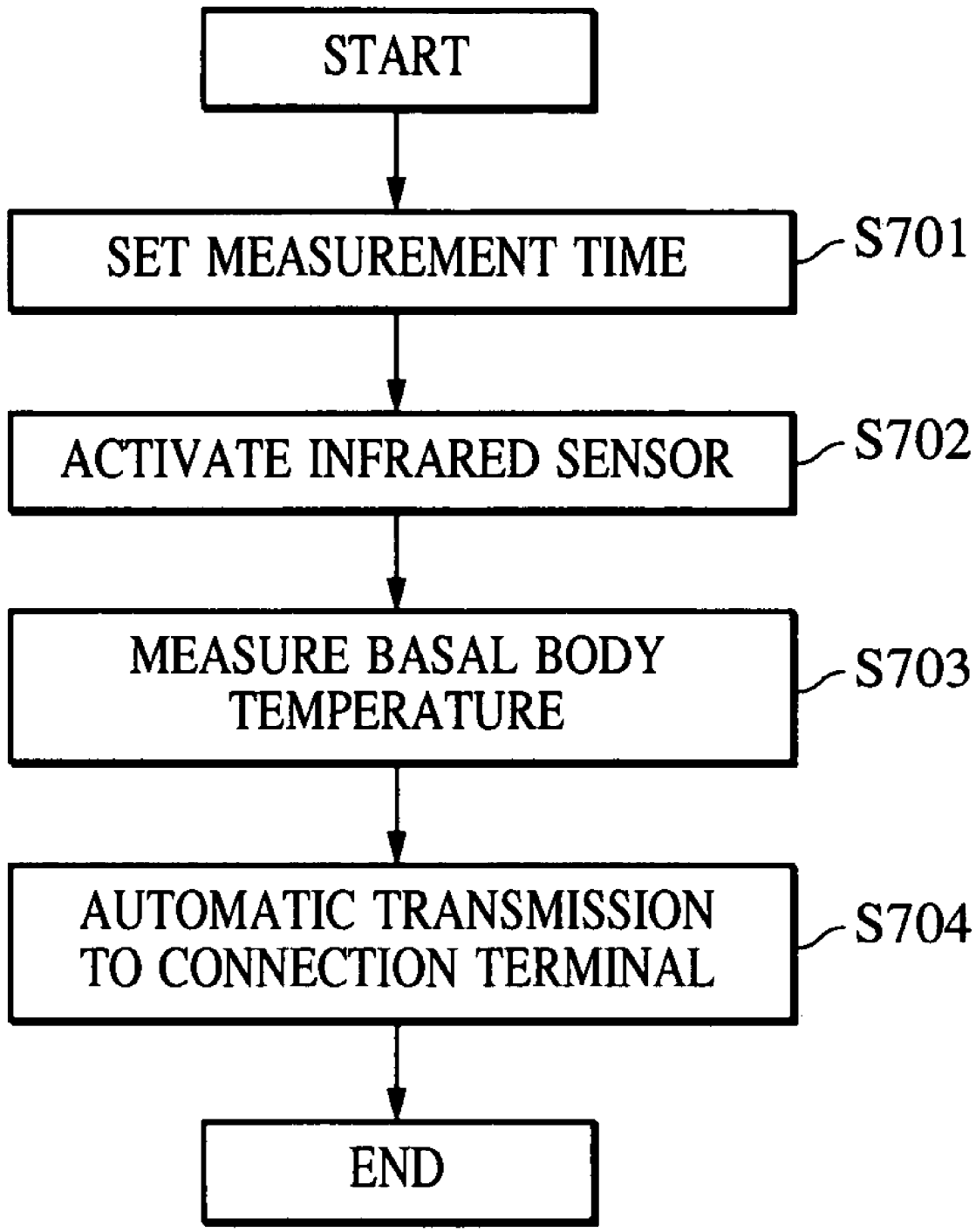
FIG. 7 is a flowchart illustrating the flow for measuring basal body temperature.

FIG. 7 is a diagram illustrating the procedures for measuring the basal body temperature. In step S701, following setting the measuring time with the timer 301 of the basal body temperature thermometer A 300, the subject wears the thermometer in her ear at the time of going to bed. In step S702, the infrared sensor 602 is activated at the set time. In step S703, the basal body temperature at the eardrum is measured by the infrared sensor 302. In step S704, the basal body temperature measured by the control unit 305 is converted into data, and is automatically transmitted to the connection terminal A 310 by the wireless device 303.

Figure 8:
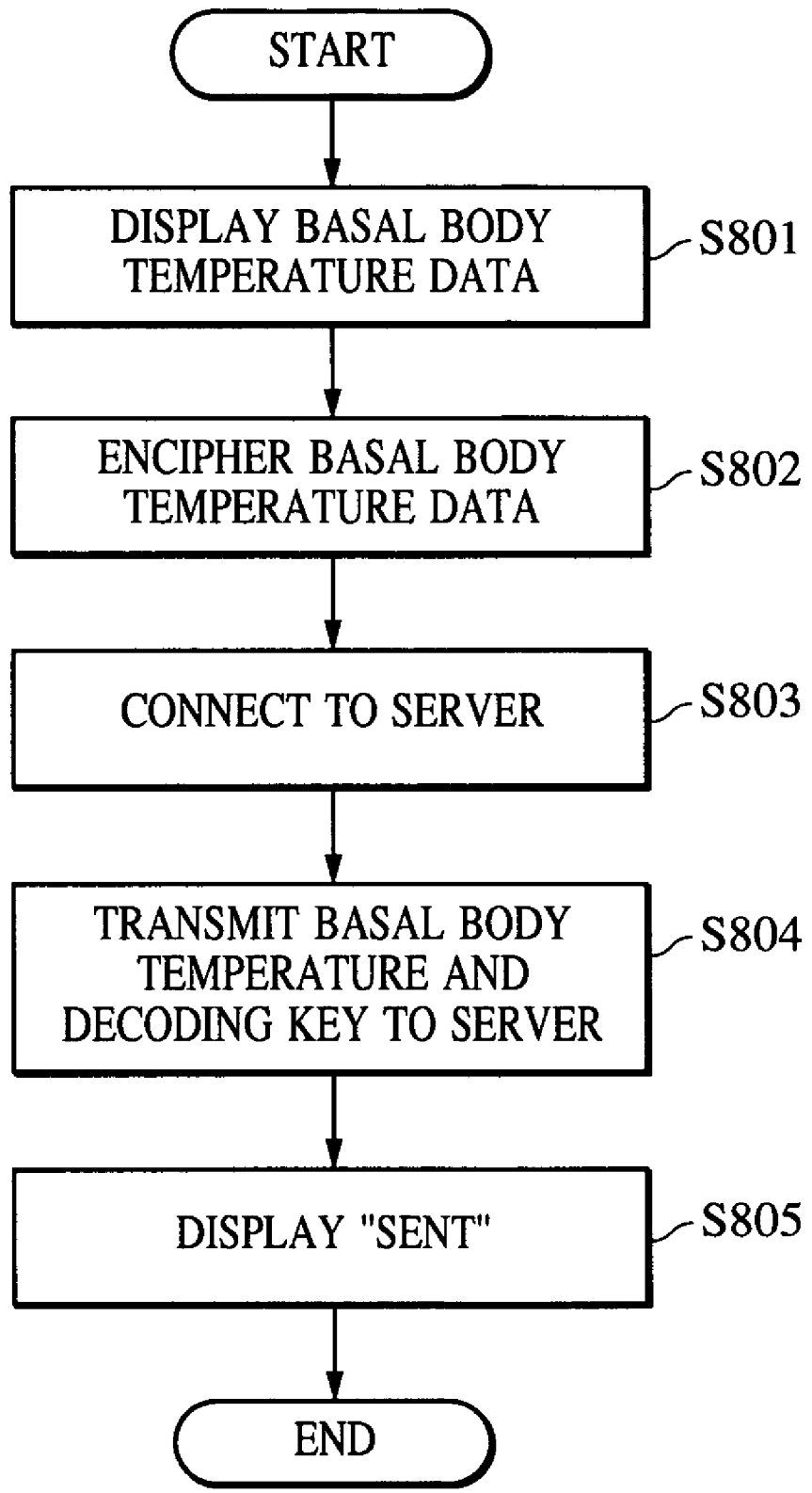
FIG. 8 is a flowchart illustrating the flow for automatically transmitting basal body temperature to a server.
Figure 9:
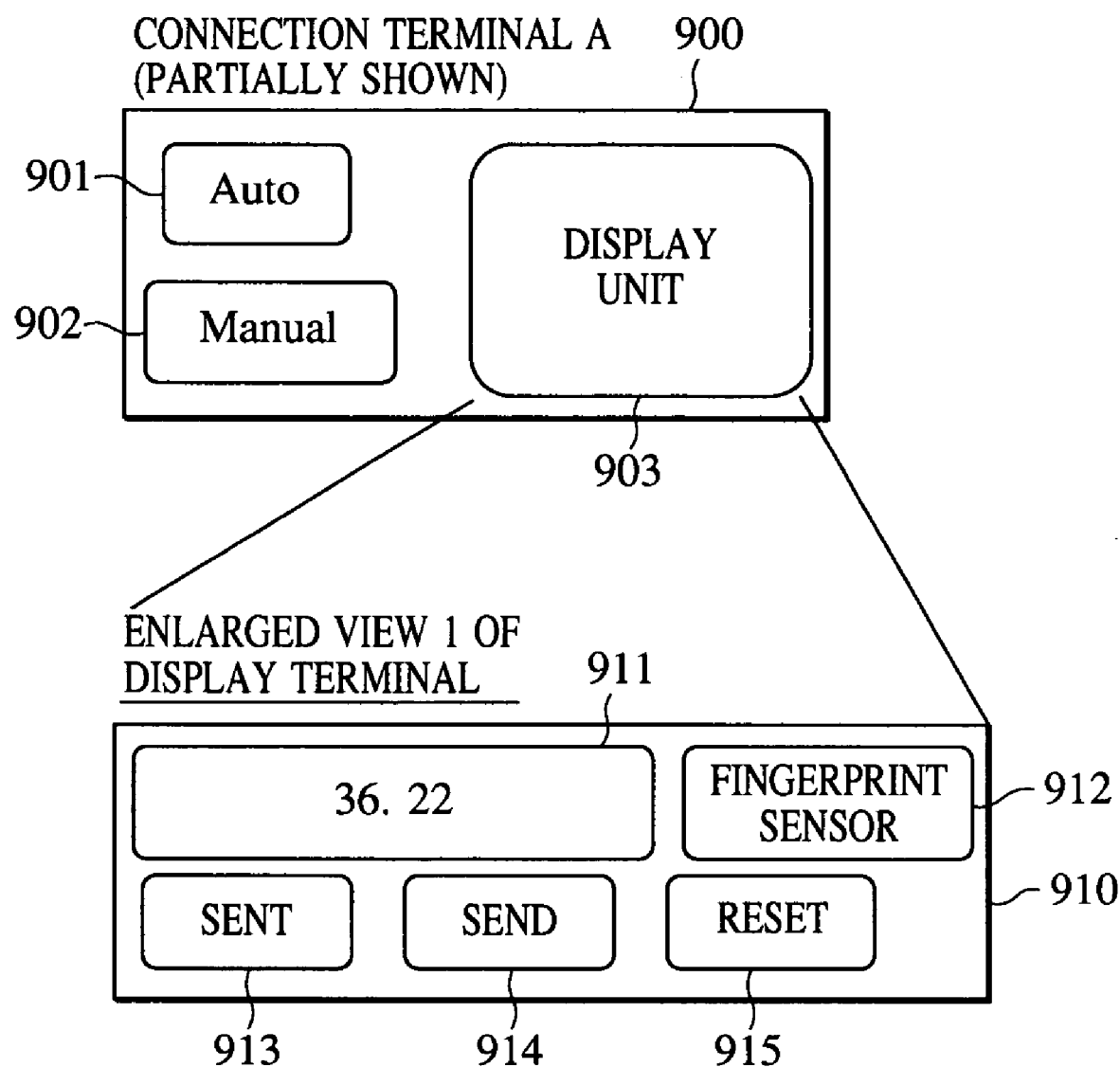
FIG. 9 is a diagram illustrating a display on a terminal device for transmitting basal body temperature to the server.

FIG. 8 is a diagram illustrating the flow for automatically transmitting basal body temperature to the server, and FIG. 9 is a diagram illustrating the display at the terminal device for transmitting the basal body temperature to the server. This automatic transmitting to the server 101 consists of measuring the basal body temperature at a time set beforehand by the subject, and automatically transmitting this from the connection terminal A 310 to the server, so that the subject can omit the procedure of making transmission to the server 101. To this end, the subject sets "Auto" 901 in the display screen denoted by 900, shown in FIG. 9. Reference numeral 900 in FIG. 9 denotes an enlarged view of the display portion indicated by reference numeral 315 in FIG. 3, and an enlarged view of the portion denoted by reference numeral 903 is shown, denoted by reference numeral 910.

The flow of making automatic transmission of basal body temperature will be described with reference to FIG. 8. In step S801, the measured basal body temperature is displayed digitally on the display unit 903 of the connection terminal, as shown by 900 in FIG. 9. In step S802, the basal body temperature is enciphered by the control unit 305 of the connection terminal A 310. In step S803, the send button 914 is automatically activated, and connection is made to the server. In step S804, the enciphered basal body temperature data is transmitted to the server along with the deciphering key. Once the transmission is completed, a sent sign denoted by reference numeral 913 is lit. In the event that a connection cannot be made due to problems on the telephone line or the like, a redial function can redial multiple times. Also, the basal body temperature displayed in step S801 remains displayed until stored in the memory 314 and the reset button 915 is pressed, so the subject can confirm this along with the sent sign 913 at the time of rising. The sent sign can be turned off by pressing the reset button 915.

Figure 10:
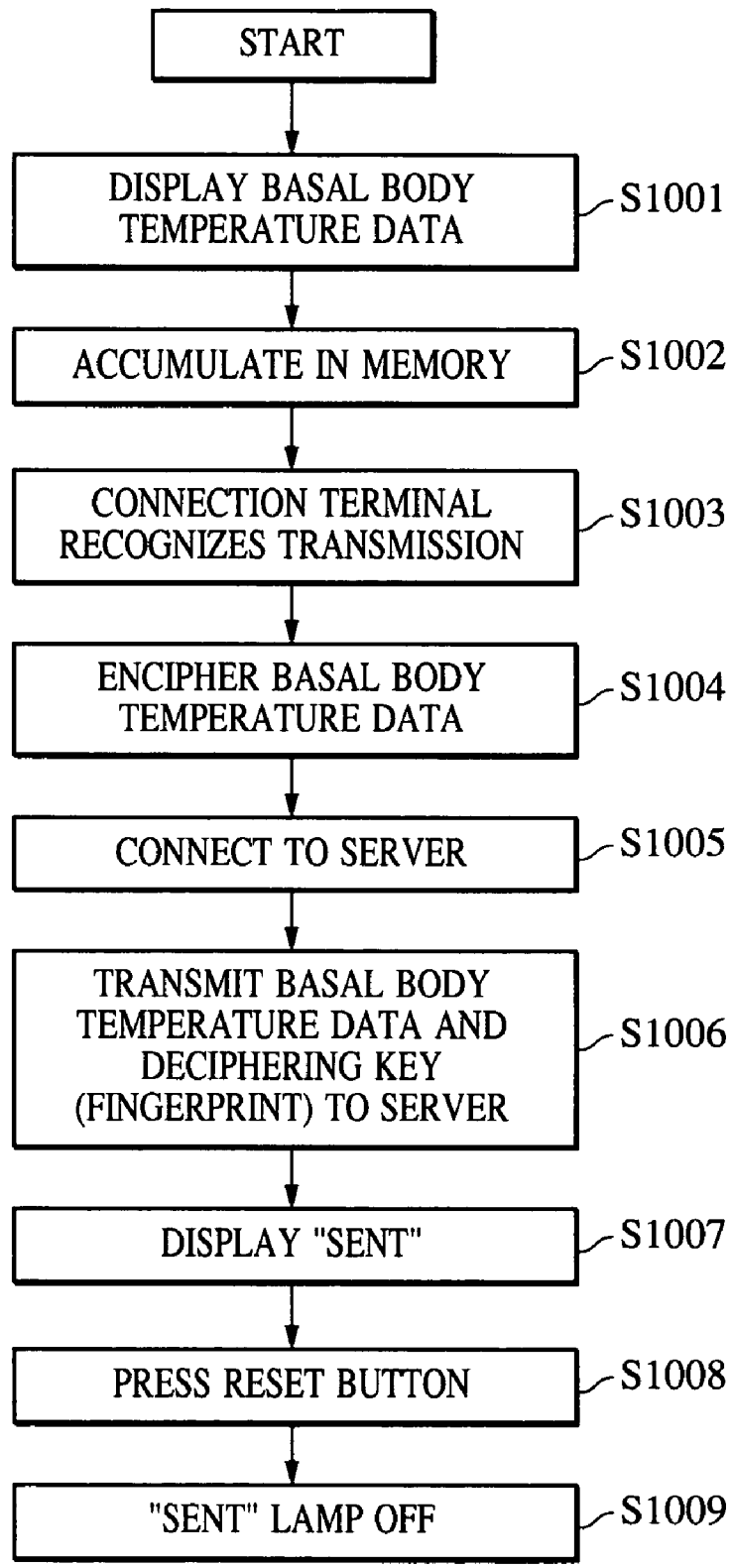
FIG. 10 is a flowchart illustrating the flow for manually transmitting basal body temperature to the server.

FIG. 10 is a diagram illustrating the flow in the event of manually transmitting the basal body temperature to the server. First, in order to transmit manually, the subject selects "Manual" indicated by the reference numeral 902 in FIG. 9. In the case of manual transmission, the manual sending button 902 on the display unit 900 is lit.

The flow for manually transmitting the basal body temperature will be described with reference to FIG. 10. In step S1001, the measured basal body temperature is digitally displayed on the display unit 903 of the connection terminal A 310 indicated by reference numeral 900 in FIG. 9, and in step S1002, the basal body temperature is stored in the memory 314. At this point, the raw data for the basal body temperature is stored in the memory 314, and this is not enciphered until the send button 914 is pressed. Several days worth of data can be accumulated in the memory 314, and can be sent in batch fashion to the server 101 later, which is handy since the subject can transmit the data later at one time even when taking a trip, etc. Also, the telephone bill for connecting to and accessing the server 101 can be conserved. Thus, providing the connection terminal A 310 with storage functions serves as means effective for markedly reducing troublesome procedures regarding basal body temperature measurement.

In step S1003, pressing the send button 914 causes the connection terminal A 310 to restrict transmission instructions. In step S1004, the basal body temperature data is enciphered. In step S1005, the line is connected via the modem 312. The send button 914 continues to blink as long as the line is connected. In step S1006, the enciphered basal body temperature data is transmitted along with the deciphering key wherein the fingerprint has been digitized. In step S1007, at the time of transmission to the server 101 ending, the sent sign is lit, thereby allowing the subject to confirm that the data has been transmitted. The sent sign can be turned off by pressing the reset button 915.

Though the present embodiment is described with an arrangement wherein the basal body temperature is enciphered at the time of transmission, the basal body temperature may be enciphered at the time of completing measurement, so that enciphered data is accumulated.

Further, though the present embodiment is described with an arrangement wherein the data is transmitted following measurement, the data may be transmitted in real-time.

Figure 4:
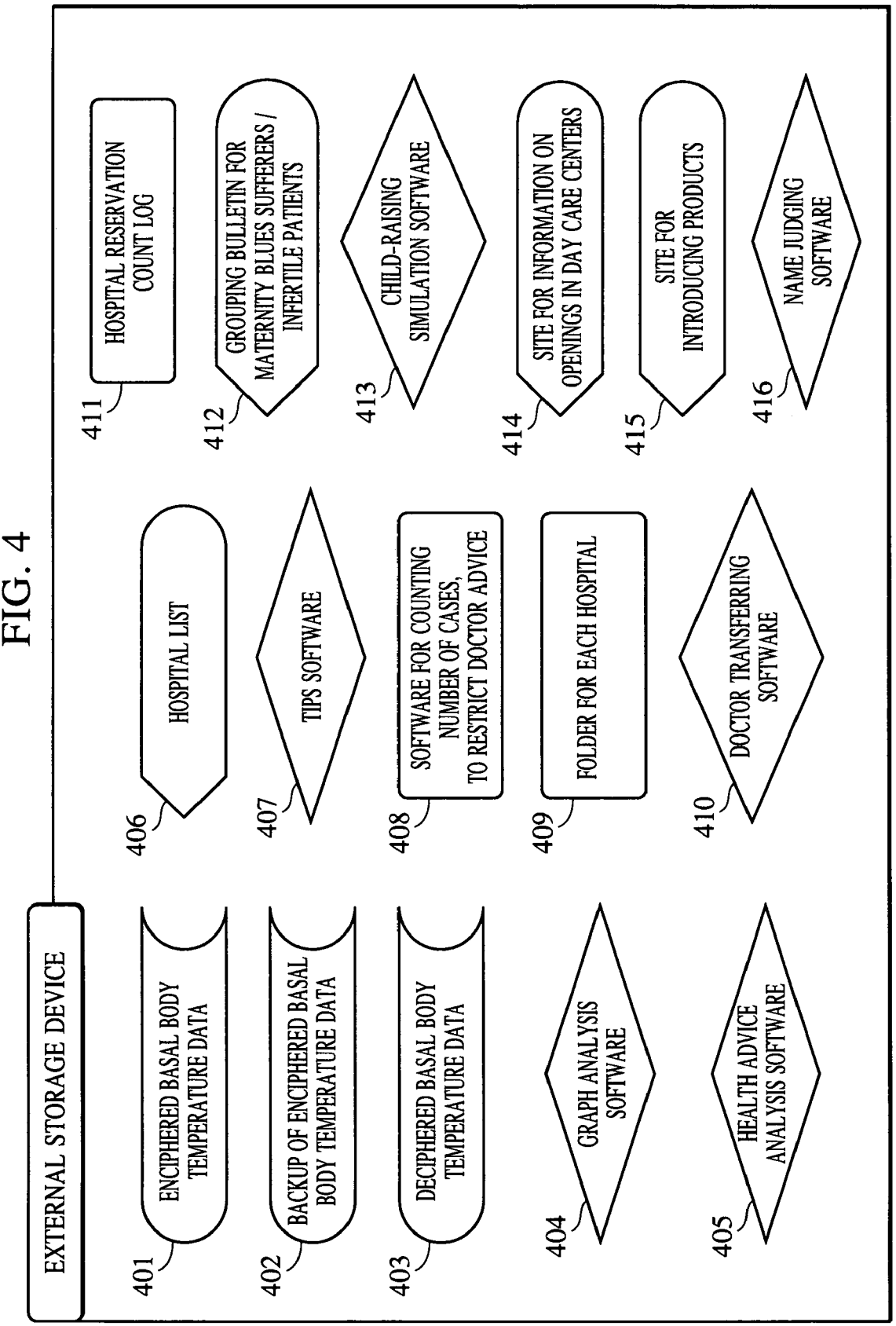
FIG. 4 is a diagram illustrating data stored in an external storage device according to an embodiment of the present invention.

FIG. 4 is a diagram illustrating the data stored in the external storage device. Reference numeral 401 denotes a storage area for storing enciphered basal body temperature data transmitted from the basal body temperature thermometer A, 402 denotes an area for storing backup data of the enciphered basal body temperature data in 401, 403 denotes an area for storing deciphered basal body temperature data, 404 denotes graph analyses software used for the graph analysis results obtaining service, 405 denotes health advice analysis software used for the health advice service, 406 denotes a hospital list used for the doctor advice obtaining service, 407 denotes tips software used with the tips service, 408 denotes software for counting number of cases to restrict doctor advice for the doctor advice obtaining service, 409 denotes folders for each of the hospitals, created at the time of signing contracts with each of the hospitals, to be used for the doctor advice obtaining service, 410 doctor transfer software used for the doctor advice obtaining service, 411 denotes a hospital reservation count log used for the doctor advice obtaining service, 412 denotes a grouping bulletin used for the maternity blues sufferers/infertile patients grouping service, 413 denotes child-raising simulation software used for the child-raising simulation service, 414 denotes an area where information relating to a site for information on openings in day care centers, for the service for information on openings in day care centers, 415 denotes an area where information relating to a site for introducing products, for the products introducing service, and 416 denotes name judging software used for the name judging service.

The details of each set of data will be described later at the time of describing each service. Also, the data stored in the external storage device 204 is by no means restricted to the data shown in FIG. 4; rather, data corresponding to various services can be stored.

(Services)

Figure 11:
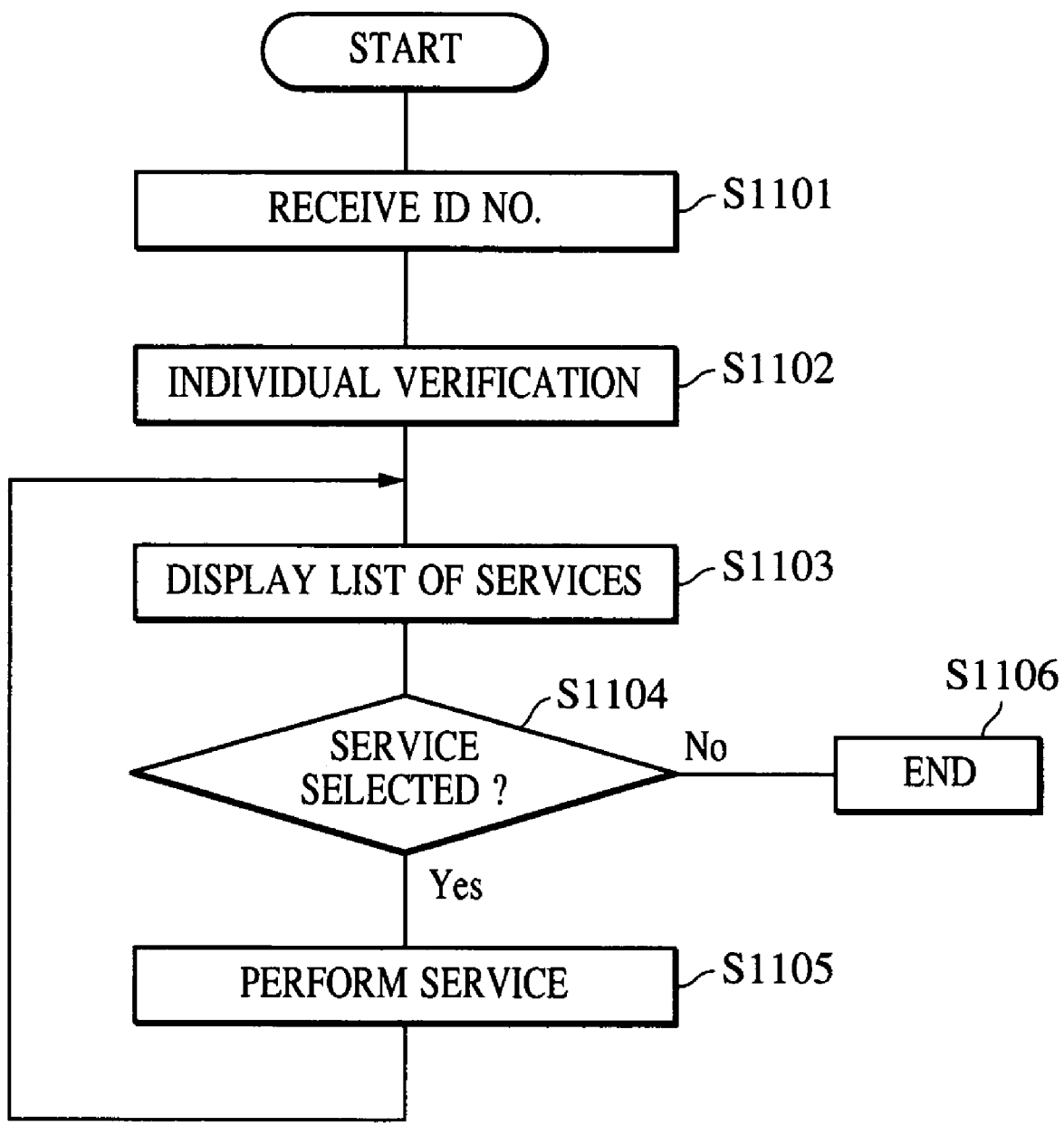
FIG. 11 is a flowchart illustrating the flow of various services according to an embodiment of the present invention.
Figure 12:
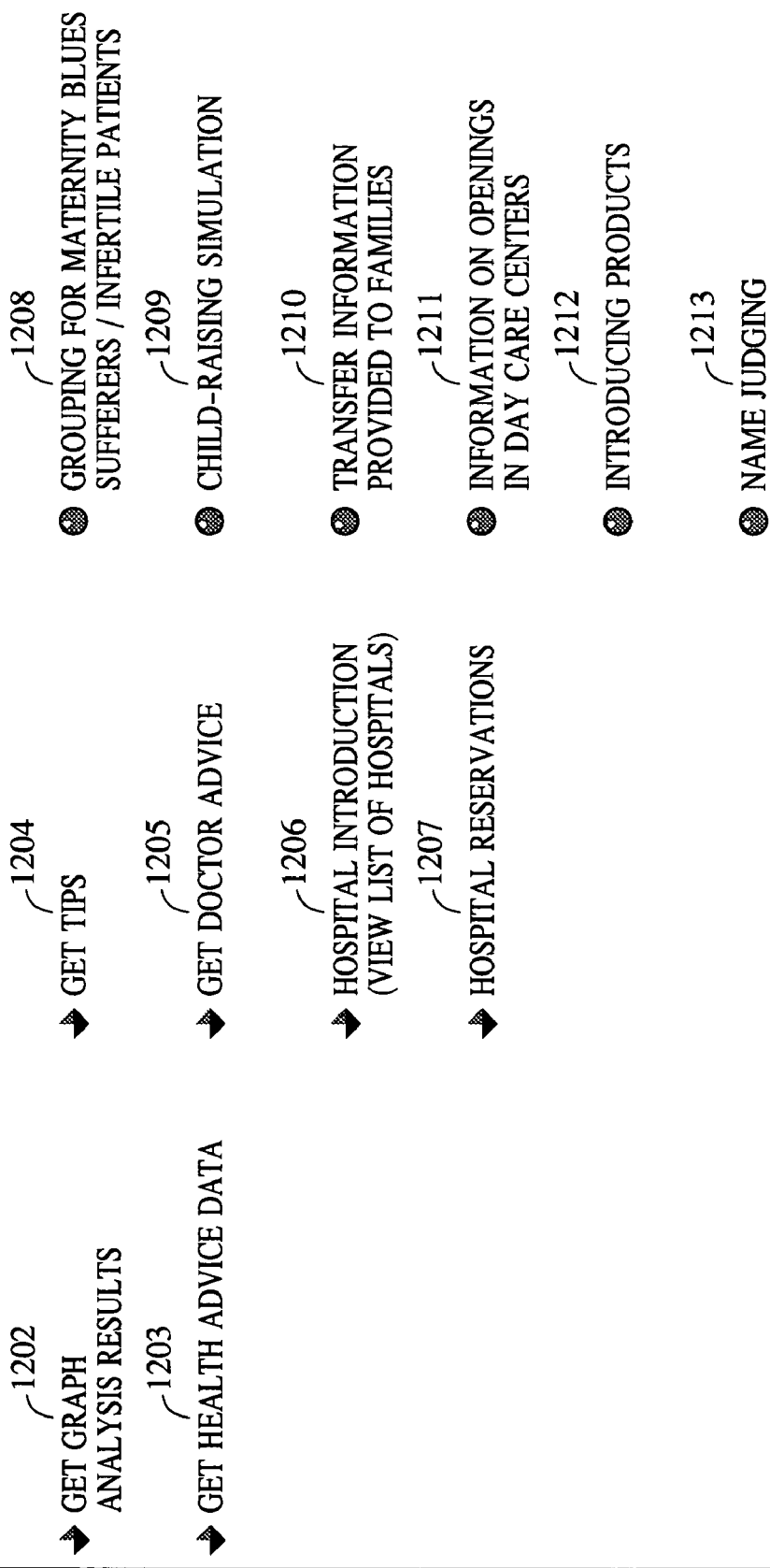
FIG. 12 is a diagram illustrating a list of services.

Next, the services using the basal body temperature thermometer according to the present invention will be described. FIG. 11 is a diagram illustrating the flow for executing the services. In step S1101, the ID No. provided with the basal body temperature thermometer, which the subject desiring to receive services has input from the subject terminal 102, is received. In step S1102, the server receives the input ID No. from the subject, and makes verification of the subject desiring to receive services. In step S1103, a list of services denoted by reference numeral 1201 in FIG. 12 is displayed. In step S1104, the subject selects a desired service from the list of services. In the event that one is selected, the flow proceeds to step S1105, and the service which the subject has selected is executed. The contents of service execution will be described later. In the event that the subject selects Cancel instead of a service in step S1104, the processing ends.

(Graph Analysis Results Obtaining Service)

Figure 13:
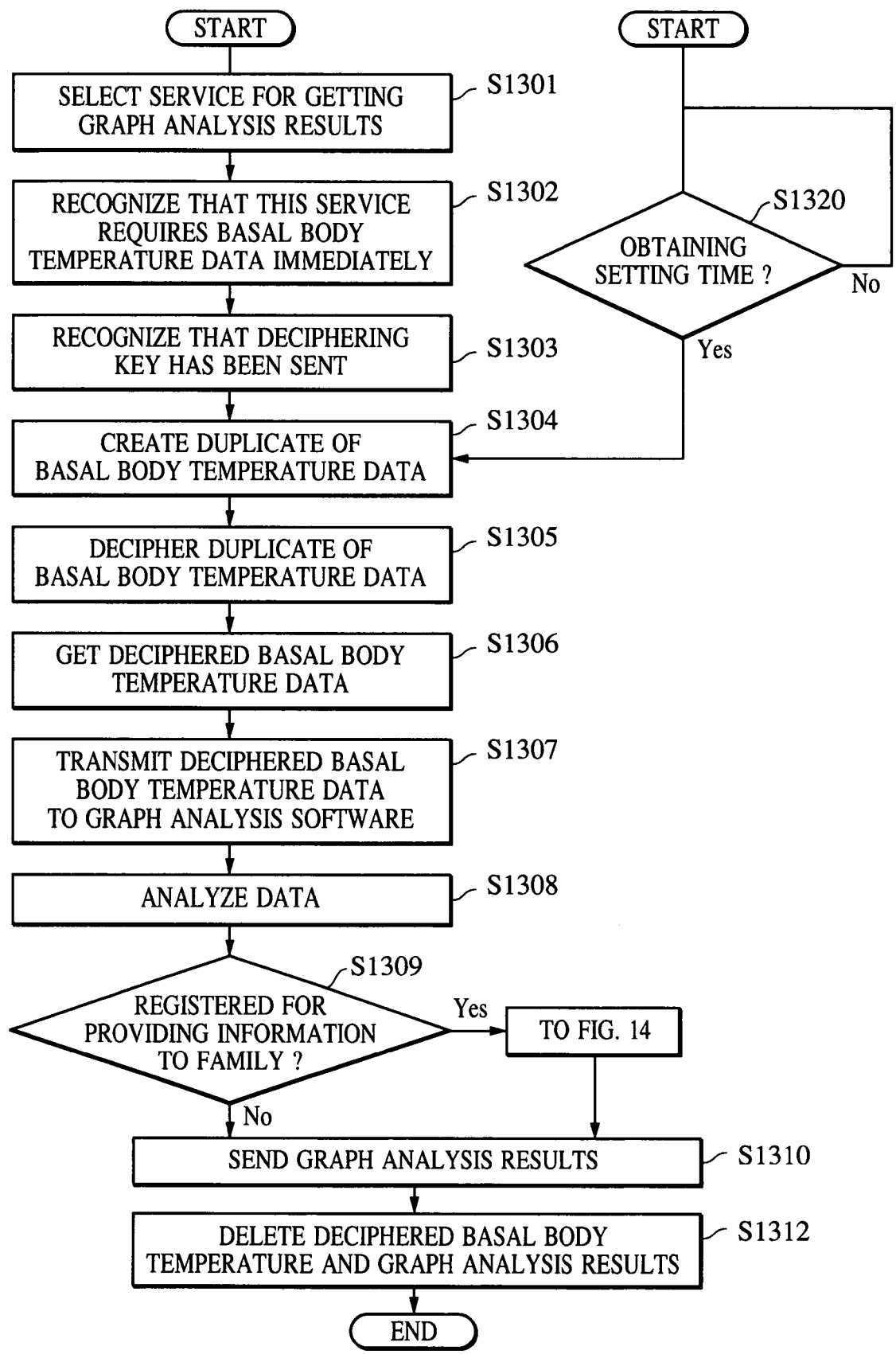
FIG. 13 is a diagram illustrating the flow for obtaining graph analysis results for basal body temperature.

FIG. 13 is a diagram illustrating the flow of a service for obtaining the results of graph analysis. First, description will be made regarding a case wherein the subject arbitrarily selects the graph analysis results obtaining service. In the event of receiving this service, in step S1301 the subject selects the Graph analysis results obtaining service, denoted by reference numeral 1202 in the list of services shown in FIG. 12 (step S1104 in FIG. 11). In step S1302, the server recognizes that this is a service which requires basal body temperature data immediately. In step S1303, the subject sends to the server the deciphering key wherein the fingerprint has been digitally converted, and the server recognizes that the deciphering key has been sent. Once the server recognizes that the deciphering key has been sent, the flow proceeds to step S1304, and a duplicate of the enciphered basal body temperature data accumulated in the server is created. In step S1305, the duplicate of the basal body temperature data thus created is deciphered based on the deciphering key that has been sent. In step S1306, the deciphered basal body temperature data is obtained.

In step S1307, the recognized basal body temperature data is transferred to the graph analyzing software. At this time, the arrangement is such that the deciphered basal body temperature data denoted by reference numeral 403 does not remain in the deciphered basal body temperature data area denoted by 403 in FIG. 4. In step S1308, the transferred basal body temperature data is analyzed. In step S1309, in the event that the subject has registered beforehand for a service to transfer to family, the server recognizes that that the subject has registered for the service to transfer to family, and the registered destination for transfer is displayed. In the event that the subject has not registered beforehand for the service to transfer to family, the flow proceeds to step S1310, and the graph analysis results are transmitted to the subject. In the event that the subject is registered for the service for transfer to family, the graph analysis results are transmitted to the subject, and also are transmitted to the registered destination for transfer. In step S1312, in order to effectuate protection from external leakage of information, the deciphered basal body temperature data and graph analysis results are deleted following transmission of the graph analysis results.

Figure 14:
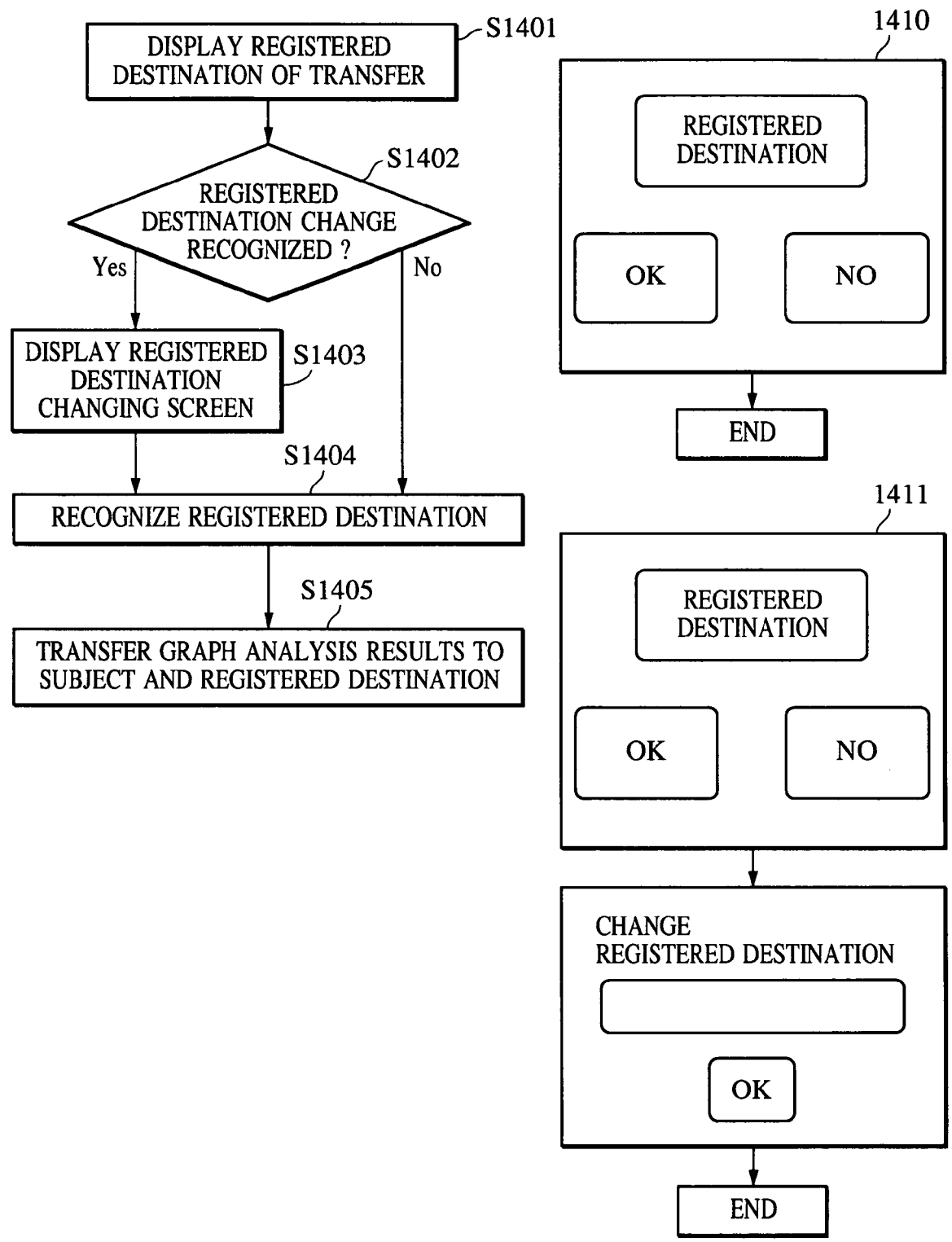
FIG. 14 is a diagram illustrating the flow and method for a service for transferring to family.

FIG. 14 illustrates the flow and registration method for the service for providing and transferring information to family. In step S1401, the registered destination of transfer is displayed on the subject terminal 102. In the event that the server recognizes change to the registered destination in step S1402, a registered destination change screen 1411 is displayed on the subject terminal 102 in step S1403, and the registration destination is recognized at the server in step S1404. In the event that the server recognizes no change to the registered destination in step S1402, the registration destination is recognized at the server in step S1404. In step S1405, the graph analysis results are transferred to the subject and to the registered destination. Note that this registered destination may be registered to persons other than family, or may also be registered to a separate terminal of the subject.

Next, description will be made regarding a service wherein the subject does not select the Graph analysis results obtaining service, but rather the analysis results are transmitted at a predetermined time. In step S1320, when the time set for obtaining the graph analyses results comes, a duplicate of the enciphered basal body temperature data is automatically created by the server (step S1304), and the duplicate of the basal body temperature data is deciphered (step S1305). Now, the time set here is imagined to be a predetermined daily time, such as 6 o'clock AM for example, but the time may be set and then set to come at predetermined intervals such as every 24 hours or every 48 hours, for example. In the following description, the flow is the same as the case wherein the subject arbitrarily selects the graph analysis results obtaining service, and thus description thereof will be omitted. After the graph analysis results are sent to the subject, the subject is prompted whether or not she would like to use other services. In the event that the server recognizes intent to obtain other services, the list of services shown in FIG. 12 is displayed again, and in the event that the server recognizes no such intent, the present service system ends.

Figure 15:
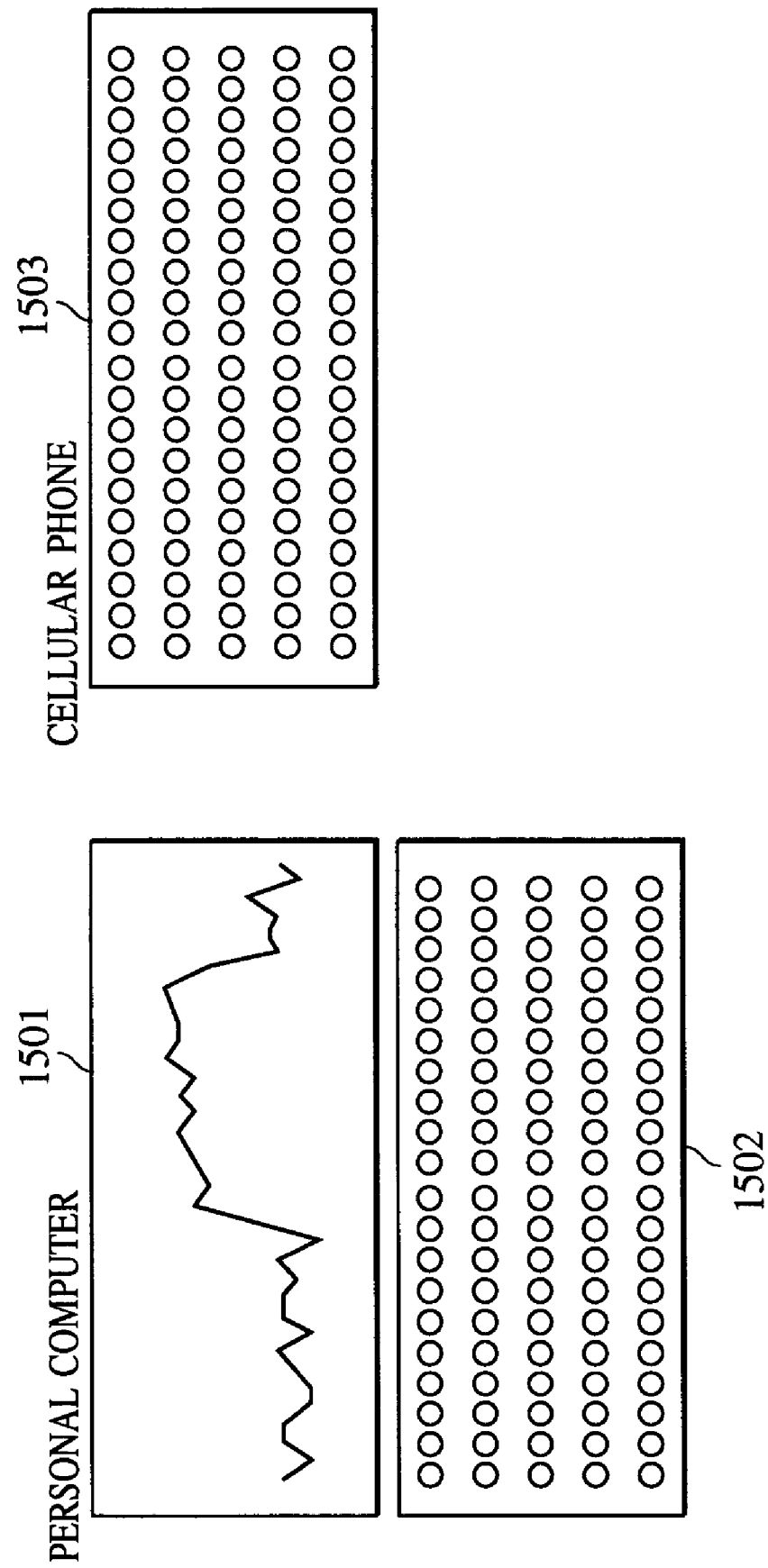
FIG. 15 is a conceptual diagram of a screen for viewing the various services.

FIG. 15 is a screen displayed on the terminal 102 of the subject, showing the screen for viewing the services. Reference numeral 1501 denotes a graph of the measured basal body temperature, and 1502 is a conceptual representation of the analysis results of the services in text. In the event of viewing the services on a personal computer, the analysis results are displayed as graph and text as indicated by 1501 and 1502. Reference numeral 1503 denotes a conceptual representation of the analysis results of the services in text alone. With terminals such as cellular phones or the like wherein display of images might be difficult, the display may be made in text alone. Examples of the contents of the text might include displays such as "ovulation on MM/DD", "currently in high-temperature phase", and so forth.

(Health Advice Data Obtaining Service)

Figure 16:
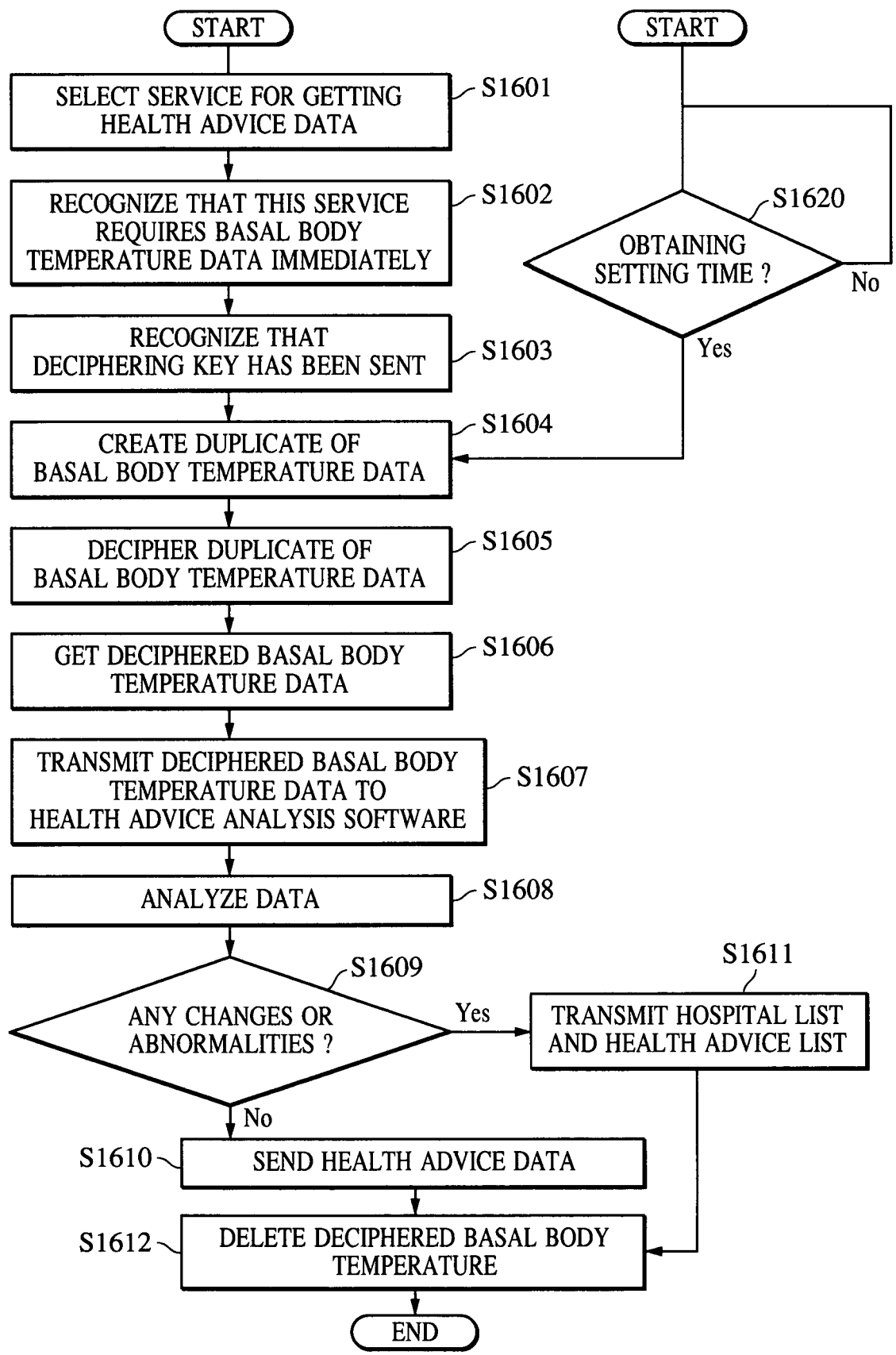
FIG. 16 is a flowchart illustrating the flow of a service for obtaining health advice data.

FIG. 16 is a diagram illustrating the flow for the Health advice data obtaining service. This service is for cases wherein the subject desires data in further detail than the above-described Graph analysis data obtaining service. In step S1601, the subject selects the Health advice data obtaining service, denoted by reference numeral 1203, from the list of services shown in FIG. 12. The flow from step S1602 through S1606 is the same as the flow from step S1302 through S1306 in FIG. 13, and accordingly description thereof will be omitted here.

In step S1607, the server 101 transmits the deciphered basal body temperature data to the health advice analysis software. At this time, the arrangement is such that the deciphered basal body temperature data does not remain in the deciphered basal body temperature data area denoted by 403 in FIG. 4, following transmitting thereof. In step S1607, the server 101 analyzes the deciphered basal body temperature data with the health advice analysis software. In step S1609, the server 101 judges whether or not there are any physical changes or abnormalities in the conditions of the body, based on the results analyzed with the health advice analysis software. Normally, the health advice data is sent to the subject (step S1610), but in the event that the analysis results show changes or abnormalities such as indications of pregnancy or the like, a URL for a hospital list 406 is transmitted to the personal computer or the cellular phone of the subject, along with the health advice data (step S1611). Upon receiving the URL of the hospital list 406, the subject can further receive the later-described hospital introduction and hospital reservation services. Following transmission of the data, the deciphered basal body temperature data and the health advice data are deleted from the server 101. After the health advice data is sent to the subject, the subject is inquired regarding whether or not she would like to use other services. In the event that the server recognizes intent to obtain other services, the list of services shown in FIG. 12 is displayed again, and in the event that the server recognizes no such intent, the present service system ends.

(Tips Service)

Figure 17:
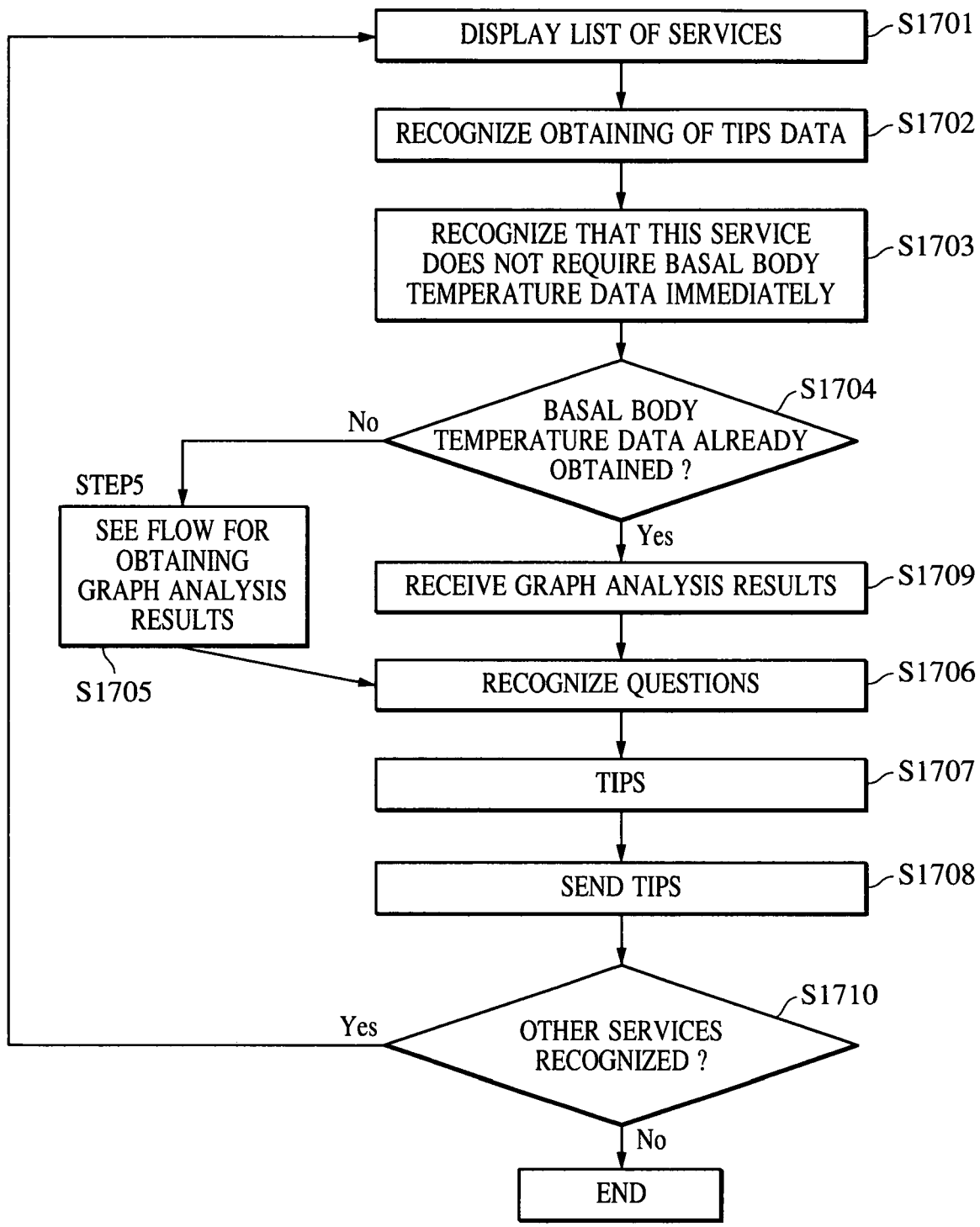
FIG. 17 is a flowchart illustrating the flow of a service for obtaining tips.

FIG. 17 is a diagram illustrating the flow of a service for obtaining brief tips with the tips software. In step S1701, list of services shown in FIG. 12 is displayed by the server. In the event that the subject selects the tips service, denoted by reference numeral 1204 in the list of services, the server recognizes in step S1702 that the tips service has been selected. In step S1703, the server recognizes that this is a service which does not immediately require basal body temperature data.

In step S1704, the server checks whether or not the subject has already obtained the basal body temperature data, and if so, the server receives the graph analysis results from the subject in step S1709, and the flow proceeds to step S1706. If not, the flow jumps to the Graph analysis results obtaining service shown in FIG. 13, and upon obtaining the graph analysis results, the flow proceeds to step S1706. In step S1706, in the event that selection of prepared questions is recognized, the tips software is activated in step S1707. Multiple sample graphs are prepared beforehand with this software, and judgment is made regarding the state of the graph of a field relating to the question of the subject, upon comparison thereof. In step S1708, the results of the tips software are transmitted to the subject. Once sent to the subject, the tips are deleted from the server. In the event that execution of another service is recognized in step S1710, the flow proceeds to that other service, and in the event that this is not recognized, the flow ends.

(Doctor Advice Service)

Figure 18:
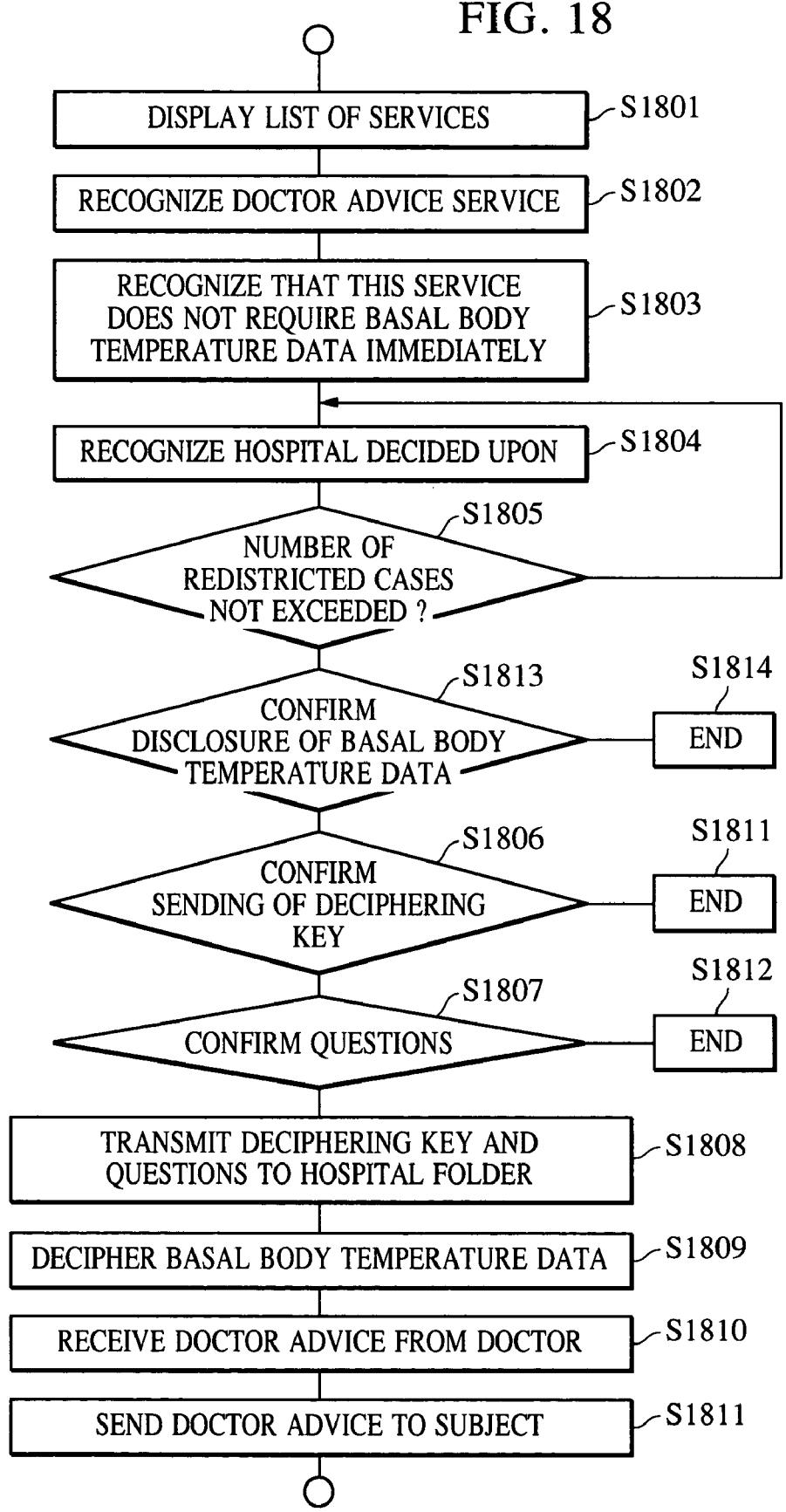
FIG. 18 is a flowchart illustrating the flow of a doctor advice service.
Figure 20:
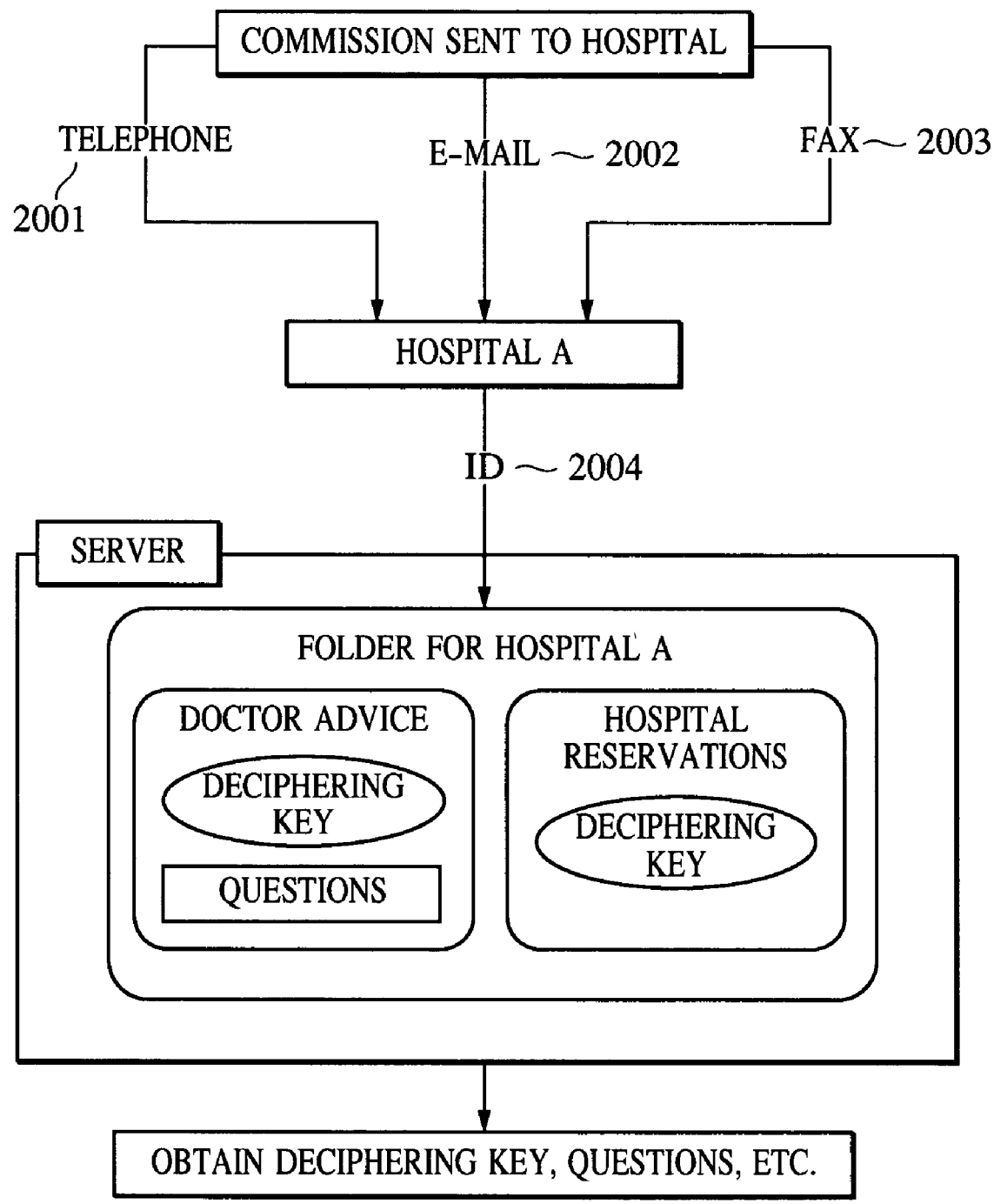
FIG. 20 is a diagram illustrating transferring to a hospital for the doctor advice service.

FIG. 18 is a flowchart illustrating the flow of the doctor advice service, FIG. 19 is a display screen for the doctor advice service, and FIG. 20 is a diagram illustrating the transfer of the doctor advice service to a hospital. The doctor advice service allows a doctor to view the basal body temperature data without the subject directly going to a hospital, and thus accurate doctor advice can be obtained. FIG. 18 illustrates the flow of operations made by the server for this doctor advice service.

In step S1801, the list of services is displayed by the server, and the subject selects the doctor advice service, denoted by reference numeral 1205, from the list. In step S1802 the server receives information indicating that the subject has selected the doctor advice service, and thus the server recognizes that the subject has selected the doctor advice service. In step S1803, the server recognizes that this is a service which does not immediately require basal body temperature data. In step S1804, the hospital which the subject has selected from the registered hospitals is recognized. Selection of the hospital may be performed by selecting a hospital from a hospital list provided in the later-described hospital introduction list, or a family doctor may be selected beforehand, provided that this family doctor is registered with the present system. In step S1805, the system checks whether or not the restricted number of cases registered by the hospital has been exceeded. Each hospital is limited in the number of cases that the hospital can deal with, so there is the need to manage the number of cases that each hospital is capable of dealing with, in order to accurately and speedily provide individual advice from doctors. In the event that this restricted number of cases has been exceeded, the subject must attempt selection of a different hospital. In the event that this restricted number of cases has not been exceeded, confirmation is made in step S1805 with the subject regarding whether or not to disclose the basal body temperature data, and whether or not to transmit the deciphering key to the hospital (1901 and 1902). Then, as indicated by 1903, the deciphering key is input by the subject, and the deciphering key is transmitted by instructing transmission of the deciphering key, as indicated by 1904. In the event that consent to transmit is not obtained, the processing ends (step S1811).

In step S1807, confirmation is made with the subject regarding whether or not there are any questions for the doctor. In step S1808, any questions are transmitted to the folder 409 for the hospital within the server, which was created at the time of signing the contract with the hospital. The doctor transfer software 410 within the server recognizes that there has been a commission for this server, and this is transferred to the doctor by a method such as; ① vocal notification by telephone (2001), ② notification by e-mail/voice mail (2002), ③ notification by facsimile, and so forth, as shown in FIG. 20. Once the doctor recognizes that there has been commission of the present service, the doctor inputs the hospital ID No. (2004) appropriated at the time of contract, which enables the doctor to view the folder 409 for the hospital to which the doctor belongs, and to recognize the deciphering key and questions of the subject (2005).

In step S1809, the hospital inputs the recognized deciphering key, and upon individual verification succeeding, a backup is created of the enciphered basal body temperature data accumulated in the server, the backup data is transferred to the hospital folder and deciphered with the deciphering key. The doctor makes a diagnosis by viewing the deciphered basal body temperature data and the questions, and creates doctor advice data. In step S1810, the server receives the doctor advice, and in step S1811, the received doctor advice is transmitted to the subject. The doctor advice data and the deciphered basal body temperature data are deleted from the server following transmission to the subject, in order to thoroughly protect from external leaking out.

Though the present embodiment has been described with reference to an arrangement wherein the subject selects the hospital, an arrangement may be made wherein the subject registers beforehand desired conditions for a hospital, and the server selects a hospital matching the conditions from the hospital list.

Also, though the present embodiment has been described with reference to an arrangement wherein the doctor views the basal body temperature data in the hospital folder located in the server, an arrangement may be made wherein the basal body temperature data is transmitted to a terminal at the hospital, where the doctor views the data.

Also, an arrangement may be made wherein the doctor can view not only the basal body temperature data, but also data obtained from the Graph analysis results obtaining service, and so forth.

(Hospital Introduction Service)

Figure 21:
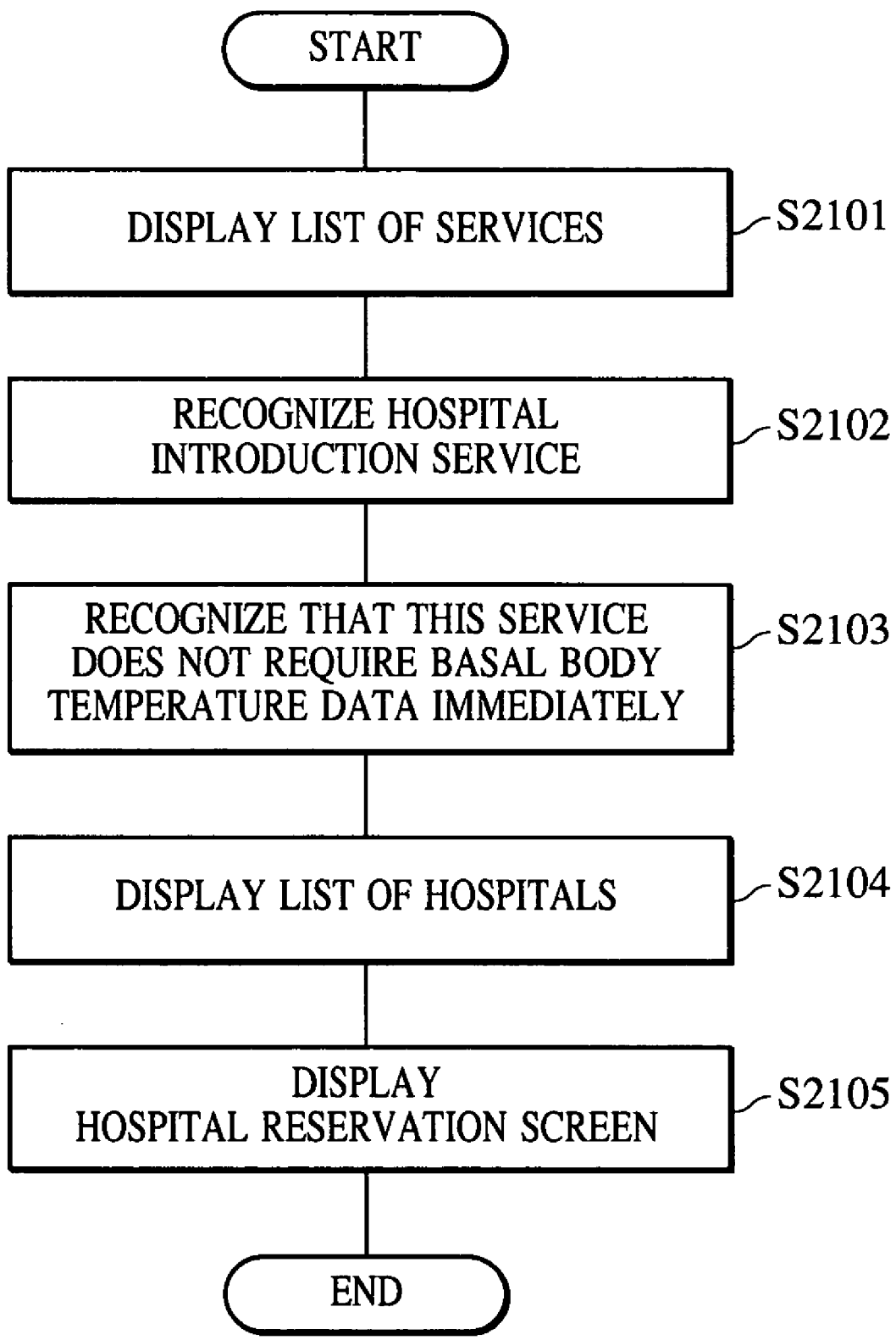
FIG. 21 is a flowchart illustrating the flow of a hospital introduction service.

FIG. 21 is a flowchart illustrating the flow of the Hospital introduction service (viewing a hospital list). In step S2101, the server instructs displaying the list of the services shown in FIG. 12. The subject selects the Hospital introduction service denoted by reference numeral 1206 from the list display of the services. In step S2102, the server recognizes that the subject has selected the Hospital introduction service. In step S2103, the server recognizes that this is a service which does not immediately require basal body temperature data. This brings up displays for restricting the area, denoted by reference numerals 2301 and 2302 in FIG. 23, and a hospital list for that area (406, 2303) is displayed in step S2104. In step S2105, the hospital reservation screen denoted by reference numeral 2304 in FIG. 23 is displayed.

Note that the hospital list may be a list display of individual hospitals, or may be a list display of individual doctors.

(Hospital Reservation Service)

Figure 22:
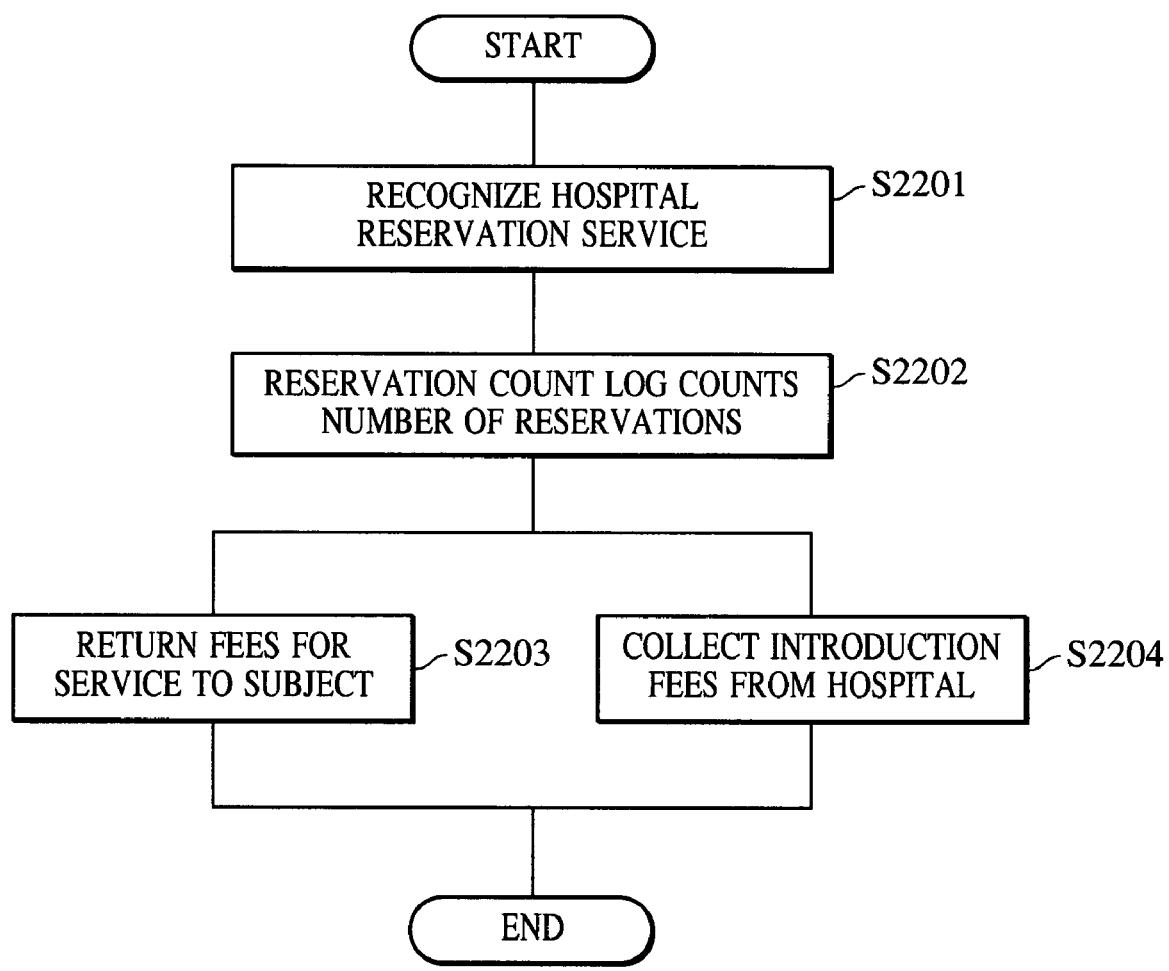
FIG. 22 is a flowchart illustrating the flow of a hospital reservation service.

FIG. 22 is a flowchart illustrating the flow of the Hospital reservation service. The subject selects the Hospital reservation service denoted by reference numeral 1207 from the list of services shown in FIG. 12, or arrives at this point via the above-described Health advice data obtaining service or Hospital introducing service, whereby a hospital list is displayed. In step S2202, in the event that the server recognizes that the subject has made a hospital reservation selection from the hospital list 406, the hospital reservation count log 411 of the server counts the number of reservations in step S2202. Depending on the number of reservations, cash is returned to the subject from the service fees at the time of the automatic bank transfer made each month, in step S2203, and in step S2204 introduction fees are collected from the hospital monthly.

(Maternity Blues Sufferers/Infertile Patients Grouping Service)

Figure 24:
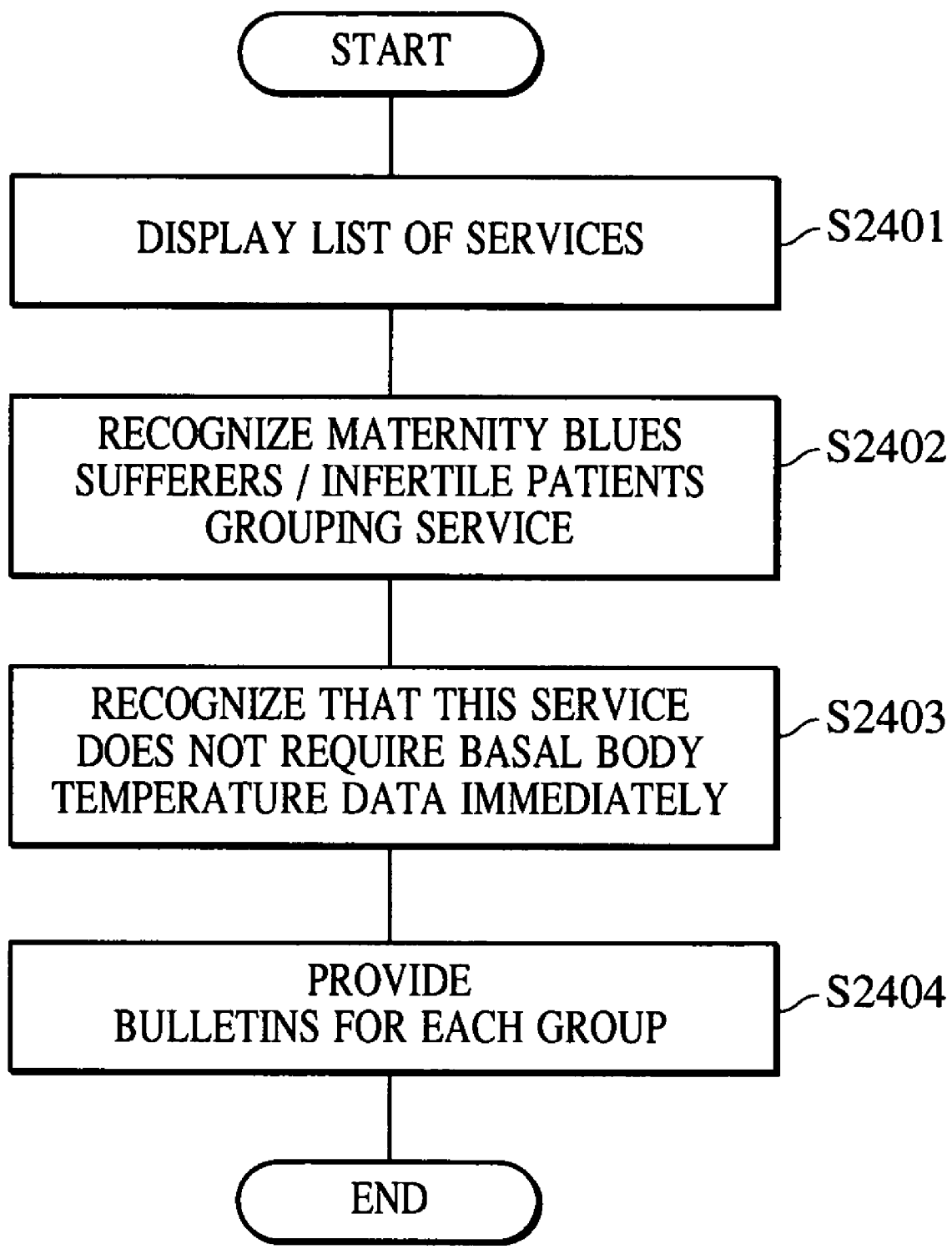
FIG. 24 is a flowchart illustrating the flow of a "grouping for maternity blues sufferers/infertile patients" service.

FIG. 24 is a flowchart illustrating the flow of the Maternity blues sufferers/infertile patients grouping service. In step S2401, the server displays the list of services shown in FIG. 12. In the event that the subject selects the Maternity blues sufferers/infertile patients grouping service denoted by reference numeral 1208 from the list display of services in FIG. 12, in step S2402 the server recognizes that the subject has selected the Maternity blues sufferers/infertile patients grouping service. In step S2403, the server recognizes that this is a service which does not immediately require basal body temperature data. In step S2404, the server provides bulletins to the groups.

(Child-raising Simulation Service)

Figure 25:
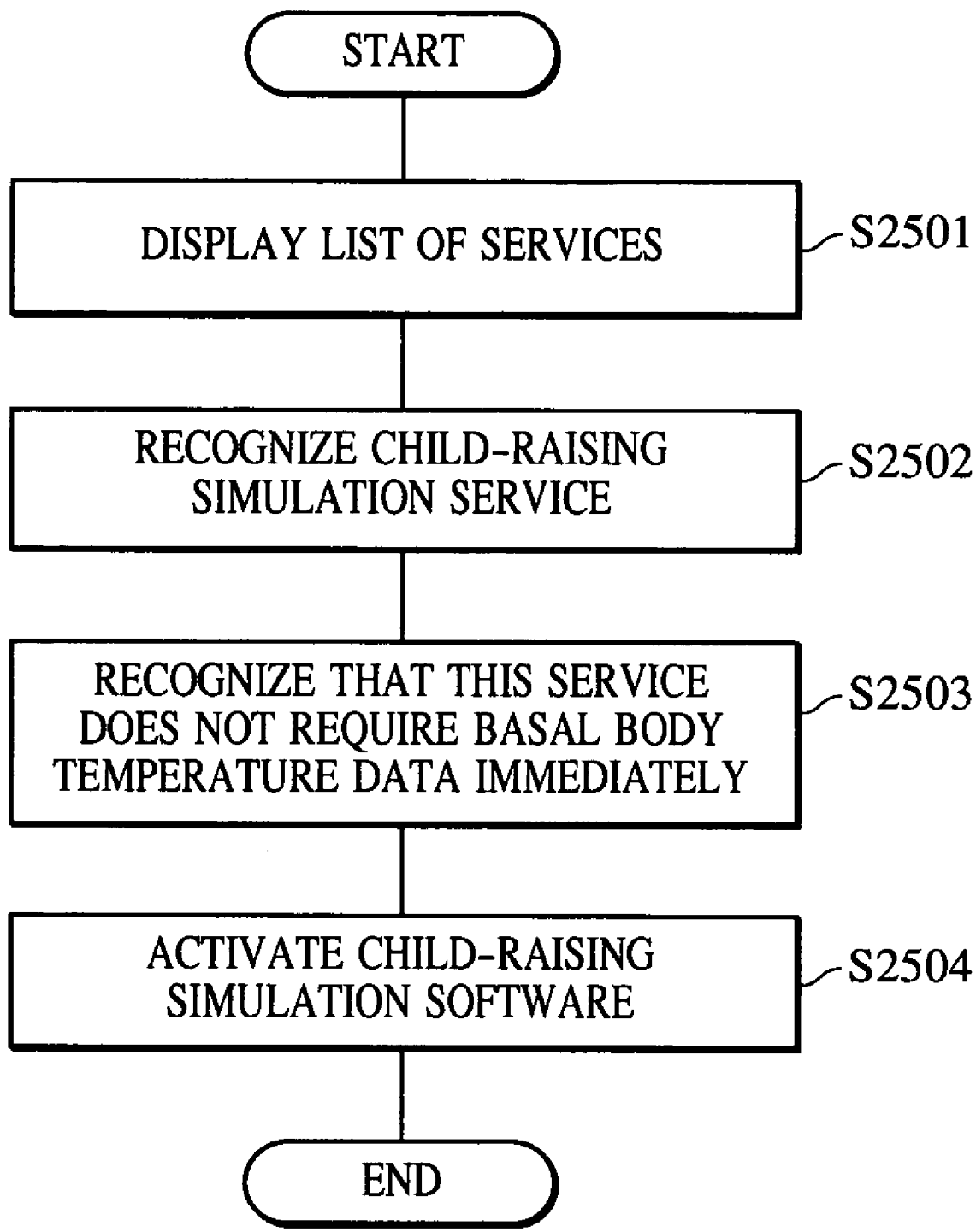
FIG. 25 is a flowchart illustrating the flow of a child-raising simulation.

FIG. 25 is a flowchart illustrating the flow of the Child-raising simulation service. In step S2501, the server displays the list of services shown in FIG. 12. In the event that the subject selects the Child-raising simulation service denoted by reference numeral 1209 from the list display of services in FIG. 12, in step S2502 the server recognizes that the subject has selected the Child-raising simulation service. In step S2503, the server recognizes that this is a service which does not immediately require basal body temperature data. In step S2504, the server activates the child-raising simulation software.

(Service for Information on Openings in Day Care Centers)

Figure 26:
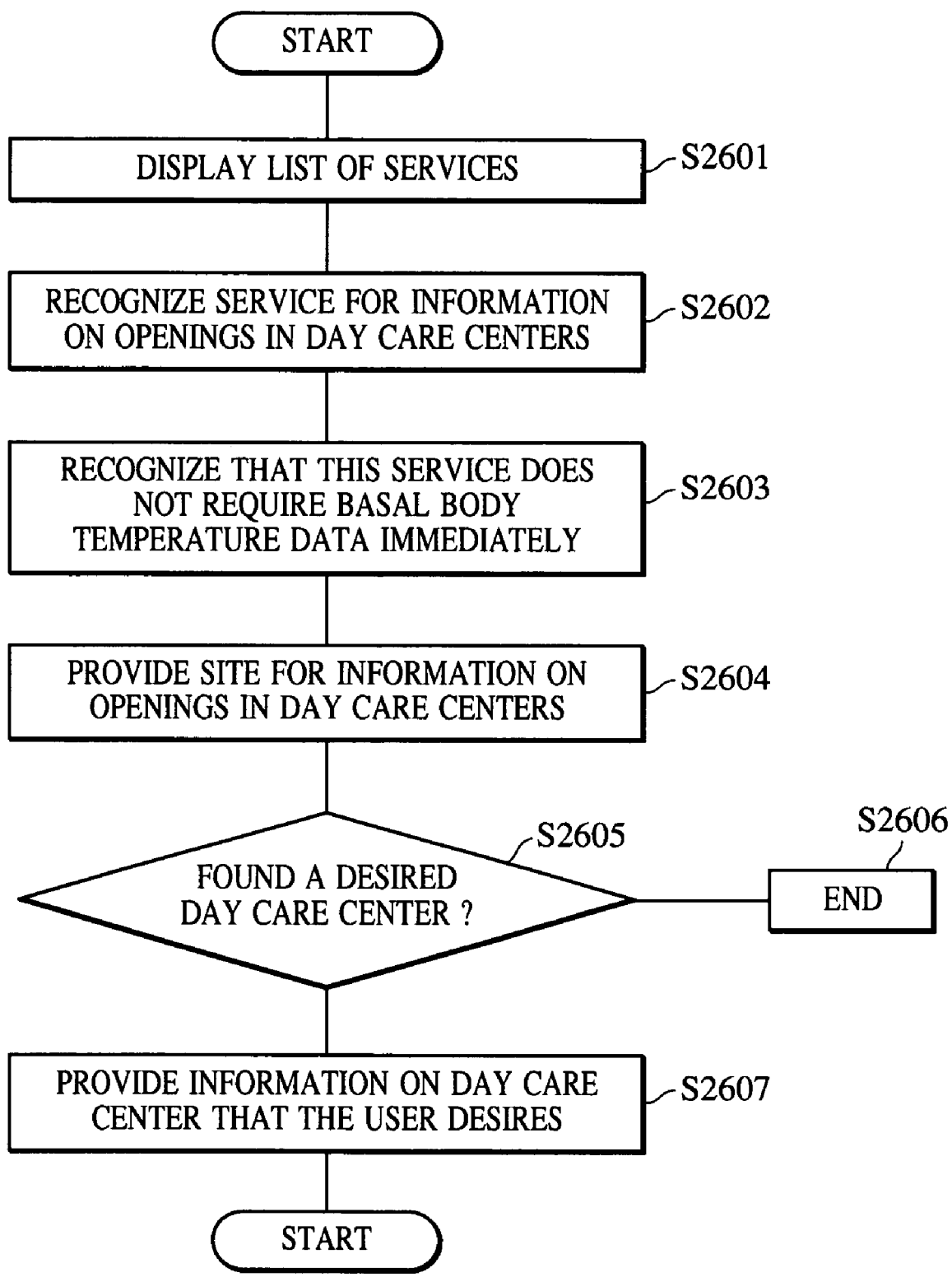
FIG. 26 is a diagram illustrating the flow of a service for information on openings in day care centers.

FIG. 26 is a flowchart illustrating the flow of the Service for information on openings in day care centers. In step S2601, the server displays the list of services shown in FIG. 12. In the event that the subject selects the Service for information on openings in day care centers, denoted by reference numeral 1211 from the list display of services in FIG. 12, in step S2602 the server recognizes that the subject has selected the Service for information on openings in day care centers. In step S2603, the server recognizes that this is a service which does not immediately require basal body temperature data. In step S2604, the server presents a site for information on openings in day care centers. In the event that the user selects a day care center in step S2605, in step S2606 the server presents the information of that day care center to the subject, and otherwise, the flow ends at step S2606.

(Products Introduction Service)

Figure 27:
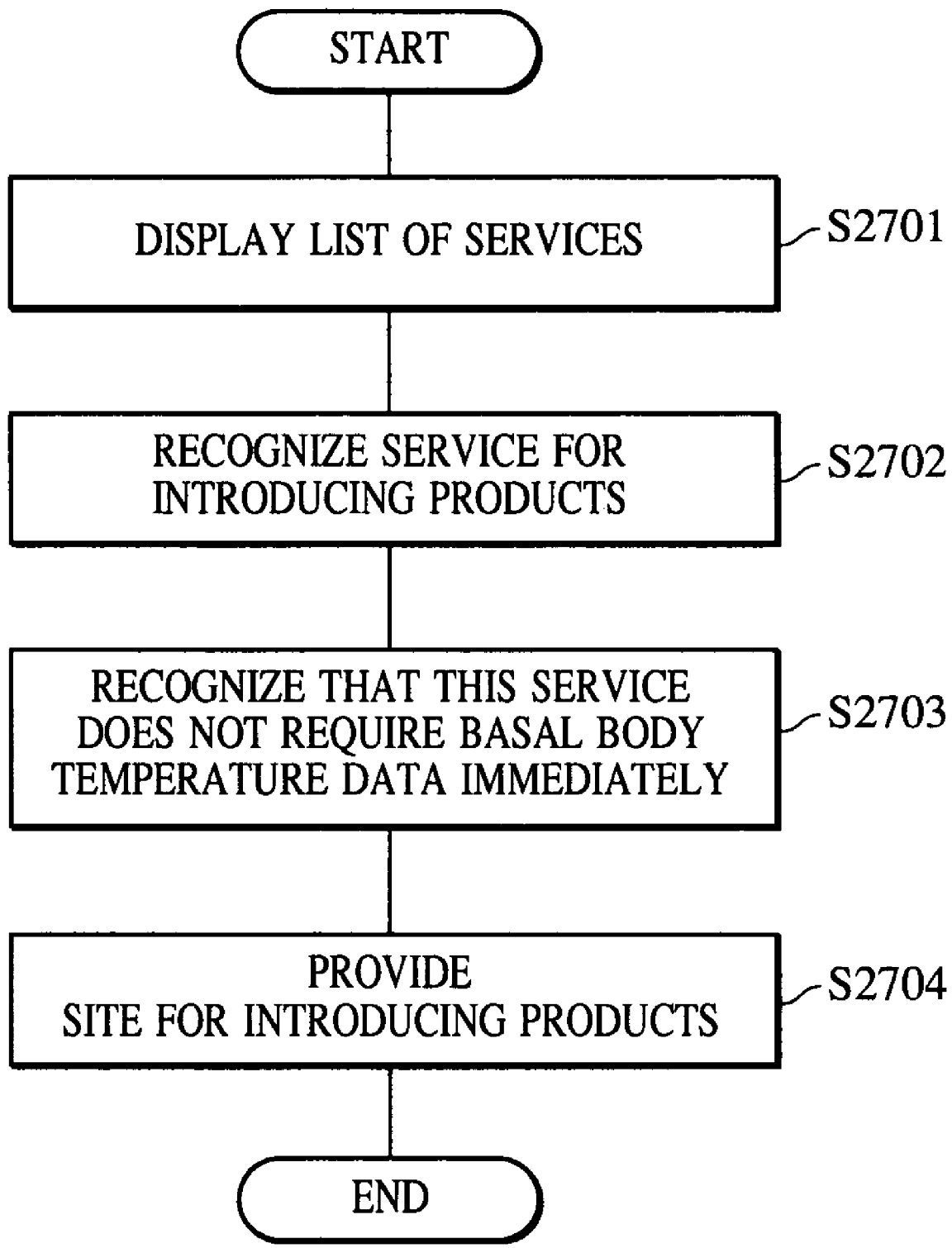
FIG. 27 is a diagram illustrating the flow of a service for introducing products.

FIG. 27 is a flowchart illustrating the flow of the Products introduction service. In step S2701, the server displays the list of services shown in FIG. 12. In the event that the subject selects the Products introduction service denoted by reference numeral 1212 from the list display of services in FIG. 12, in step S2702 the server recognizes that the subject has selected the Products introduction service. In step S2703, the server recognizes that this is a service which does not immediately require basal body temperature data. In step S2704, the server displays a Products introduction site.

(Name Judging Service)

FIG. 28 is a flowchart illustrating the flow of the Name judging service. In step S2801, the server displays the list of services shown in FIG. 12. In the event that the subject selects the Name judging service denoted by reference numeral 1213 from the list display of services in FIG. 12, in step S2802 the server recognizes that the subject has selected the Name judging service. In step S2803, the server recognizes that this is a service which does not immediately require basal body temperature data. In step S2804, the server activates the name judging software.

In this way, the present system is not restricted to data analysis of basal body temperature data, but rather is capable of providing the subject with detailed health data with health advice analysis software, tips based on data comparison, and further is capable of tying in with hospitals to provide hospital information, systematic hospital reservations, doctor advice from sent basal body temperature data, and so forth, in order to aim for more effective health management.

Also, services which can be provided include subject grouping services wherein infertile patients or pregnant individuals can communicate with individuals in the same state, systematic information on openings in day care centers for individuals who want to put their child in a day care center after birth, introduction of products, name judging systems, child-raising simulations, transfer of information to family, and so forth, i.e., overall services relating to basal body temperature can be provided.

Of course, the arrangement may be such that anyone can use the services which do not require basal body temperature data, not only subjects.

Also, simple body temperature may be used instead of basal body temperature.

Also, means for recording dates of menstruation may be provided to record this along with the basal body temperature.

Also, with regard to the services which use basal body temperature data, the past two months worth of basal body temperature data counting back from the present is used for analysis of the basal body temperature data in the initial state, but all data from the point of gaining membership may be used, or the subject or doctor may specify the period to be used, counting back from the present.

Also, though the above-described arrangement involves the list of services shown in FIG. 12 coming up at the point that a service is completed, an arrangement may be made wherein results of the service, or service menus customized for the subject, come up.

Also, though the present embodiment has been described with reference to an arrangement wherein the program is kept in ROM, the present invention is not restricted to this arrangement, and may be realized using any recording media. Also, this may be realized with a circuit acting in the same manner.

Also, the present invention can be applied to systems configured of multiple servers, or a device configured of a single server. It is needless to say that the functions of the above-described embodiments can be achieved by an arrangement wherein a recording medium storing software program code for realizing the functions of the above embodiment is supplied to the system or device, and the system or device is operated by the computer (CPU or MPU) of the system or device reading out and executing the program code stored in the recording medium. In this case, the program code itself read out from the recording medium realizes the functions of the above-described embodiment, and the recording medium storing the program code comprises the invention.

Examples of recording mediums which can be used for storing the program code include floppy disks, hard disks, optical disks, magneto-optical disks, CD-ROMs, CD-Rs, magnetic tape, non-volatile memory cards, ROM, and so forth.

Also, it is needless to say that the present invention encompasses cases not only where the computer executing the program code realizes the functions of the above embodiment, but also where the operating system or other applications running on the computer perform all or part of the actual processing based on instructions of the program code, whereby the functions of the above embodiment are realized.

Further, the scope of the present invention also encompasses arrangements wherein the supplied program code is written to memory provided to function expansion boards inserted to the computer or memory provided to function expansion units connected to the computer, following which a CPU or the like provided to the function expansion boards or function storing units performs all or part of the actual processing based on instructions of the program code, so as to realize the functions of the above embodiment thereby.

Thus, as described above, according to the present embodiment, medical management and analysis of basal body temperature data can be performed on a network while effectuating protection of private data from external leakage, and judgment and analyses based on newest information analysis, various services relating to basal body temperature data, etc., can be provided on a network, using information communication networks such as cellular phones and the Internet.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A body temperature managing method, comprising:
   a body temperature data obtaining step for obtaining body temperature data;
   a body temperature data storing step for storing said body temperature data obtained in said obtaining step;
   a body temperature data analyzing step for analyzing body temperature data based on said body temperature data stored in said storing step;
   an analyzed data transmitting step for transmitting the body temperature data analyzed in said analyzing step to an outside display device,
   wherein a display format of said analyzed body temperature data differs depending on said outside display device;
   a presenting step for presenting a list of facilities according to the analysis results analyzed in said body temperature data analyzing step;
   a counting step for counting a number of reservations, in the event that reservations have been made at an arbitrary facility from the facility list presented in said presenting step; and
   a cash-back step for giving cash back based on the counted number of reservations.

2. A body temperature managing method according to claim 1, wherein said body temperature data is basal body temperature data.

3. A body temperature managing method according to claim 1, wherein the cash-back step gives back cash to the individual making reservations, depending on said counted number.

4. A body temperature managing method according to claim 1, wherein said analyzed data transmitting step comprises a second transmitting step for transmitting analyzed data to a facility selected from said facility list presented in said presenting step, and an obtaining step for obtaining results diagnosed based on said body temperature data at said facility.

5. A body temperature managing method according to claim 1, wherein the destination of transmission of said analyzed data transmitted in said analyzed data transmitting step is one of at least a personal computer, cellular phone, or a portable terminal.

6. A body temperature managing method according to claim 1, wherein data obtained in said body temperature data obtaining step is enciphered data.

7. A body temperature managing method according to claim 1, wherein said body temperature data analyzing step further comprises a deciphering step for deciphering said body temperature data.

8. A body temperature managing method according to claim 1, wherein the transmitted body temperature data includes text data or graph and text data, depending on a size of a display area of the outside display device.

9. A body temperature managing method, comprising:
   a body temperature data obtaining step for obtaining body temperature data;
   a body temperature data storing step for storing said body temperature data obtained in said obtaining step;
   a body temperature data analyzing step for analyzing body temperature data based on said body temperature data stored in said storing step;
   an analyzed data transmitting step for transmitting the body temperature data analyzed in said analyzing step to an outside display device, wherein a display format of said analyzed body temperature data differs depending on said outside display device;
   a presenting step for presenting a list of hospitals according to the analysis results analyzed in said body temperature data analyzing step;
   a counting step for counting a number of reservations, in the event that reservations have been made at an arbitrary hospital from the hospital list presented in said presenting step; and
   a cash-back step which gives back cash to the individual making reservations, depending on said counted number.

10. A body temperature managing method, comprising:
    a body temperature data obtaining step for obtaining body temperature data;
    a body temperature data storing step for storing said body temperature data obtained in said obtaining step;
    a body temperature data analyzing step for analyzing body temperature data based on said body temperature data stored in said storing step;
    an analyzed data transmitting step for transmitting the body temperature data analyzed in said analyzing step to an outside display device, wherein a display format of said analyzed body temperature data differs depending on said outside display device;
    a presenting step for presenting a list of hospitals according to the analysis results analyzed in said body temperature data analyzing step,
    wherein said analyzed data transmitting step comprises a second transmitting step for transmitting analyzed data to a hospital selected from said hospital list presented in said presenting step, and an obtaining step for obtaining results diagnosed based on said body temperature data at said hospital;
    a counting step for counting a number of reservations, in the event that reservations have been made at an arbitrary hospital from the hospital list presented in said presenting step; and
    a cash-back step for giving cash back based on the counted number of reservations.

11. A body temperature managing method, comprising:
a body temperature data obtaining step for obtaining enciphered body temperature data;
a body temperature data storing step for storing said enciphered body temperature data obtained in said obtaining step;
a duplicate creating step for creating a duplicate of said enciphered body temperature data;
a data deciphering step for deciphering said body temperature data created in said duplicate creating step;
a body temperature data analyzing step for analyzing the body temperature data deciphered in said data deciphering step;
a deleting step for deleting said deciphered body temperature data following completion of said analyzing step;
an analyzed data transmitting step for outside transmitting of analyzed data analyzed in said analyzing step;
a presenting step for presenting a list of facilities according to the analysis results analyzed in said body temperature data analyzing step;
a counting step for counting a number of reservations, in the event that reservations have been made at an arbitrary facility from the facility list presented in said presenting step; and
a cash-back step for giving cash back based on the counted number of reservations.

12. A body temperature managing device, comprising:
body temperature data obtaining means for obtaining enciphered body temperature data;
body temperature data storing means for storing said enciphered body temperature data obtained by said obtaining means;
body temperature data analyzing means for deciphering said enciphered body temperature data stored in said storing means and for analyzing body temperature data based on the deciphered body temperature data;
analyzed data transmitting means for transmitting the body temperature data analyzed by said analyzing means to an outside display device,
wherein a display format of said analyzed body temperature data differs depending on said outside display device;
presenting means for presenting a list of facilities according to the analysis results analyzed by said body temperature data analyzing means;
counting means for counting a number of reservations, in the event that reservations have been made at an arbitrary facility from the facility list presented by said presenting means; and
cash-back means for giving cash back based on the counted number of reservations.

13. A body temperature managing device according to claim 12, wherein the transmitted body temperature data includes text data or graph and text data, depending on a size of a display area of the outside display device.

14. A body temperature managing device, comprising:
body temperature data obtaining means for obtaining body temperature data;
body temperature data storing means for storing said body temperature data obtained by said obtaining means;
body temperature data analyzing means for analyzing body temperature data based on said body temperature data stored in said storing means;
analyzed data transmitting means for transmitting the body temperature data analyzed by said analyzing means to an outside display device,
wherein a display format of said analyzed body temperature data differs depending on said outside display device;
presenting means for presenting a list of facilities according to the analysis results analyzed by said body temperature data analyzing means;
counting means for counting a number of reservations, in the event that reservations have been made at an arbitrary facility from the facility list presented by said presenting means; and
cash-back means for giving cash back based on the counted number of reservations.

15. A body temperature managing device according to one of claims 12 and 14, wherein said body temperature data is basal body temperature data.

16. A body temperature managing device according to one of claims 12 and 14, wherein the destination of transmission of said analyzed data transmitted by said analyzed data transmitting means is one of at least a personal computer, cellular phone, or a portable terminal.

17. A body temperature managing device according to claim 14, wherein the cash-back means gives back cash to the individual making reservations, depending on said counted number.

18. A body temperature managing device according to claim 14, wherein said analyzed data transmitting means comprises second transmitting means for transmitting analyzed data to a facility selected from said facility list presented by said presenting means, and obtaining means for obtaining results diagnosed based on said body temperature data at said facility.

19. A body temperature managing device according to claim 14, wherein data obtained by said body temperature data obtaining means is enciphered data.

20. A body temperature managing device according to claim 14, wherein said body temperature data analyzing means further comprises deciphering means for deciphering said body temperature data.

21. A body temperature managing device, comprising:
body temperature data obtaining means for obtaining body temperature data;
body temperature data storing means for storing said body temperature data obtained by said obtaining means;
body temperature data analyzing means for analyzing body temperature data based on said body temperature data stored in said storing means;
analyzed data transmitting means for transmitting the body temperature data analyzed by said analyzing means to an outside display device, wherein a display format of said analyzed body temperature data differs depending on said outside display device;
presenting means for presenting a list of hospitals according to the analysis results analyzed by said body temperature data analyzing means;
counting means for counting a number of reservations, in the event that reservations have been made at an arbitrary hospital from the hospital list presented by said presenting means; and
cash-back means which gives back cash to the individual making reservations, depending on said counted number.

22. A body temperature managing device, comprising:
body temperature data obtaining means for obtaining body temperature data;
body temperature data storing means for storing said body temperature data obtained by said obtaining means;

body temperature data analyzing means for analyzing body temperature data based on said body temperature data stored in said storing means;

analyzed data transmitting means for transmitting the body temperature data analyzed by said analyzing means to an outside display device, wherein a display format of said analyzed body temperature data differs depending on said outside display device;

presenting means for presenting a list of hospitals according to the analysis results analyzed by said body temperature data analyzing means, wherein said analyzed data transmitting means comprises second transmitting means for transmitting analyzed data to a hospital selected from said hospital list presented by said presenting means, and obtaining means for obtaining results diagnosed based on said body temperature data at said hospital;

counting means for counting a number of reservations, in the event that reservations have been made at an arbitrary facility from the facility list presented by said presenting means; and cash-back means for giving cash back based on the counted number of reservations.

23. A body temperature managing device, body temperature data obtaining means for obtaining enciphered body temperature data;

body temperature data storing means for storing said enciphered body temperature data obtained by said obtaining means;

duplicate creating means for creating a duplicate of said enciphered body temperature data;

data deciphering means for deciphering said body temperature data created by said duplicate creating means;

body temperature data analyzing means for analyzing the body temperature data deciphered by said data deciphering means;

deleting means for deleting said deciphered body temperature data following completion of said analyzing means;

analyzed data transmitting means for outside transmitting of analyzed data analyzed by said analyzing means;

presenting means for presenting a list of facilities according to the analysis results analyzed by said body temperature data analyzing means;

counting means for counting a number of reservations, in the event that reservations have been made at an arbitrary facility from the facility list presented in said presenting means; and cash-back means for giving cash back based on the counted number of reservations.

24. A computer-readable storage medium storing a computer-executable program, the program comprising:

program code for a body temperature data obtaining step for obtaining enciphered body temperature data;

program code for a body temperature data storing step for storing said enciphered body temperature data obtained in said obtaining step;

program code for a body temperature data analyzing step for deciphering said enciphered body temperature data stored in said storing step and for analyzing body temperature data based on the deciphered body temperature data;

program code for an analyzed data transmitting step for transmitting the body temperature data analyzed in said analyzing step to an outside display device, wherein a display format of said analyzed body temperature data differs depending on said outside display device;

program code for a presenting step for presenting a list of facilities according to the analysis results analyzed in said body temperature data analyzing step;

program code for a counting step for counting a number of reservations, in the event that reservations have been made at an arbitrary facility from the facility list presented in said presenting step; and program code for a cash-back step for giving cash back based on the counted number of reservations.

25. A computer-readable storage medium storing a computer-executable program, said program comprising:

program code for a body temperature data obtaining step for obtaining body temperature data;

program code for a body temperature data storing step for storing said body temperature data obtained in said obtaining step;

program code for a body temperature data analyzing step for analyzing body temperature data based on said body temperature data stored in said storing step;

program code for an analyzed data transmitting step for transmitting the body temperature data analyzed in said analyzing step to an outside display device, wherein a display format of said analyzed body temperature data differs depending on said outside display device;

program code for a presenting step for presenting a list of facilities according to the analysis results analyzed in said body temperature data analyzing step;

program code for a counting step for counting a number of reservations, in the event that reservations have been made at an arbitrary facility from the facility list presented in said presenting step; and program code for a cash-back step for giving cash back based on the counted number of reservations.

26. A storage medium according to one of claims 24 and 25, wherein the destination of transmission of said analyzed data transmitted in said analyzed data transmitting step is one of at least a personal computer, cellular phone, or a portable terminal.

27. A storage medium according to claim 25, wherein the cash-back step gives back cash to the individual making reservations, depending on said counted number.

28. A storage medium according to claim 25, wherein said analyzed data transmitting step comprises program code for a second transmitting step for transmitting analyzed data to a facility selected from said facility list presented in said presenting step, and program code for an obtaining step for obtaining results diagnosed based on said body temperature data at said facility.

29. A storage medium according to claim 25, wherein data obtained in said body temperature data obtaining step is enciphered data.

30. A storage medium according to claim 25, wherein said body temperature data analyzing step further comprises a deciphering step for deciphering said body temperature data.

31. A storage medium according to claim 25, wherein the transmitted body temperature data includes text data or graph and text data, depending on a size of a display area of the outside display device.

32. A computer-readable storage medium storing a computer-executable program for managing body temperature, said program comprising:

body temperature data obtaining code for obtaining enciphered body temperature data;

body temperature data storing code for storing said enciphered body temperature data obtained by said obtaining code;
duplicate creating code for creating a duplicate of said enciphered body temperature data;
data deciphering code for deciphering said body temperature data created by said duplicate creating code;
body temperature data analyzing code for analyzing the body temperature data deciphered by said data deciphering code;
deleting code for deleting said deciphered body temperature data following completion of said analyzing code;
analyzed data transmitting code for outside transmitting of analyzed data analyzed by said analyzing code;

presenting code for presenting a list of facilities according to the analysis results analyzed by said body temperature data analyzing code;

counting code for counting a number of reservations, in the event that reservations have been made at an arbitrary facility from the facility list presented in said presenting code; and cash-back code for giving cash back based on the counted number of reservations.

\* \* \* \* \*

UNITED STATES PATENT AND TRADEMARK OFFICE
CERTIFICATE OF CORRECTION

PATENT NO.         : 7,198,600 B2
APPLICATION NO.    : 09/867614
DATED              : April 3, 2007
INVENTOR(S)        : Tamaki et al.

It is certified that error appears in the above-identified patent and that said Letters Patent is hereby corrected as shown below:

COLUMN 1:
Line 55, "always-present." should read -- always present. --; and
Line 63, "obtaining" should read -- obtain --.

COLUMN 11:
Line 55, "as;" should read -- as: --.

Signed and Sealed this

Tenth Day of June, 2008

JON W. DUDAS
*Director of the United States Patent and Trademark Office*